(12) United States Patent
Hyde et al.

(10) Patent No.: US 9,443,061 B2
(45) Date of Patent: Sep. 13, 2016

(54) DEVICES AND METHODS FOR RECORDING INFORMATION ON A SUBJECT'S BODY

(75) Inventors: Roderick A. Hyde, Redmond, WA (US); Jordin T. Kare, Seattle, WA (US); Wayne R. Kindsvogel, Seattle, WA (US); Royce A. Levien, Lexington, MA (US); Erez Lieberman, Cambridge, MA (US); Mark A. Malamud, Seattle, WA (US); Nathan P. Myhrvold, Bellevue, WA (US); Elizabeth A. Sweeney, Seattle, WA (US); Clarence T. Tegreene, Bellevue, WA (US); Charles Whitmer, North Bend, WA (US); Lowell L. Wood, Jr., Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 0 days.

(21) Appl. No.: 13/199,046

(22) Filed: Aug. 16, 2011

(65) Prior Publication Data

US 2013/0046235 A1   Feb. 21, 2013

(51) Int. Cl.
*A61M 5/00* (2006.01)
*G06F 19/00* (2011.01)

(52) U.S. Cl.
CPC ......... *G06F 19/3456* (2013.01); *G06F 19/322* (2013.01)

(58) Field of Classification Search
CPC .............. A61M 2205/6063; A61M 2205/609; A61M 2205/6081; A61M 2205/3592; A61M 37/0084; A01K 11/00; A01K 11/006; A01K 11/004; A01K 11/008; A61D 1/025; G06F 19/322; G06F 19/3456; A61B 19/44; A61B 19/54; A61B 2019/446; A61B 2019/448; A61B 2019/545; A61B 2019/5437; A61B 2019/5487

USPC ........... 604/82, 116, 181, 187, 191; 606/116

See application file for complete search history.

(56) References Cited

U.S. PATENT DOCUMENTS

| | | | |
|---|---|---|---|
| 5,201,715 A | 4/1993 | Masters | |
| 5,454,045 A | 9/1995 | Perkins et al. | |
| 5,772,671 A * | 6/1998 | Harmon | 606/117 |
| 5,773,811 A | 6/1998 | Schramm, Jr. et al. | |
| 5,878,155 A | 3/1999 | Heeter | |
| 5,961,494 A | 10/1999 | Hogan | |
| 6,056,737 A | 5/2000 | Rosen | |
| 6,100,804 A | 8/2000 | Brady et al. | |
| 6,217,935 B1 | 4/2001 | Hubbell | |

(Continued)

OTHER PUBLICATIONS

Bomlai, Pornsuda; "Phase and Morphology Evolution of Sodium—Potassium Niobate Powder Synthesized by Solid-State Reaction"; pp. 1-3; printed on Aug. 9, 2011.

(Continued)

*Primary Examiner* — Laura Bouchelle

(57) ABSTRACT

Embodiments disclosed herein relate to methods, devices, and computer systems thereof for visibly or non-visibly indicating a subject has received a medical treatment. In certain embodiments, a subject receives an information mark in conjunction with a medical treatment. In certain embodiments, the information mark includes unique information relating to the subject. In certain embodiments, devices, computer systems, and methods relate to reading an information mark on a subject, and optionally determining if further medical treatment of the subject is warranted. In certain embodiments, receipt of an information mark entitles a subject to a reward.

31 Claims, 7 Drawing Sheets

(56) References Cited

U.S. PATENT DOCUMENTS

| | | | |
|---|---|---|---|
| 6,228,055 B1* | 5/2001 | Foerster et al. | 604/116 |
| 6,234,964 B1 | 5/2001 | Iliff | |
| 6,264,637 B1 | 7/2001 | Hogan | |
| 6,350,244 B1* | 2/2002 | Fisher | 600/562 |
| 6,425,764 B1 | 7/2002 | Lamson | |
| 6,436,105 B1 | 8/2002 | Passmore | |
| 6,470,891 B2 | 10/2002 | Carroll | |
| 6,526,984 B1 | 3/2003 | Nilsson et al. | |
| 6,527,750 B1 | 3/2003 | Frandsen | |
| 6,558,352 B1 | 5/2003 | Hogan | |
| 6,565,532 B1* | 5/2003 | Yuzhakov | A45D 34/04 604/142 |
| 6,565,538 B2 | 5/2003 | Quinn et al. | |
| 6,699,188 B2 | 3/2004 | Wessel | |
| 6,731,111 B2 | 5/2004 | Sawa et al. | |
| 6,923,816 B1 | 8/2005 | Passmore | |
| 6,938,488 B2 | 9/2005 | Diaz et al. | |
| 6,972,022 B1 | 12/2005 | Griffin | |
| 6,980,670 B1 | 12/2005 | Hoffman et al. | |
| 7,066,908 B2* | 6/2006 | Kuracina et al. | 604/116 |
| 7,089,498 B1 | 8/2006 | Rathjen et al. | |
| 7,181,266 B2 | 2/2007 | Frangioni et al. | |
| 7,344,587 B2 | 3/2008 | Khan et al. | |
| 7,546,955 B2 | 6/2009 | Marty et al. | |
| 7,549,960 B2 | 6/2009 | Govari | |
| 7,558,616 B2 | 7/2009 | Govari et al. | |
| 7,647,085 B2 | 1/2010 | Cane et al. | |
| 7,651,505 B2* | 1/2010 | Lubock et al. | 606/116 |
| 7,791,593 B2 | 9/2010 | Cohen et al. | |
| 7,869,011 B2 | 1/2011 | Christensen et al. | |
| 8,177,792 B2* | 5/2012 | Lubock et al. | 606/116 |
| 8,442,281 B2 | 5/2013 | Jung et al. | |
| 2001/0016696 A1 | 8/2001 | Bystrom et al. | |
| 2002/0073099 A1 | 6/2002 | Gilbert et al. | |
| 2002/0087437 A1 | 7/2002 | Hogan | |
| 2002/0158765 A1 | 10/2002 | Pape et al. | |
| 2003/0038721 A1* | 2/2003 | Hogan | 340/573.3 |
| 2003/0040706 A1* | 2/2003 | Kuracina et al. | 604/116 |
| 2003/0065294 A1 | 4/2003 | Pickup et al. | |
| 2003/0113540 A1* | 6/2003 | Anderson et al. | 428/403 |
| 2003/0135128 A1 | 7/2003 | Suffin et al. | |
| 2003/0176785 A1* | 9/2003 | Buckman et al. | 600/431 |
| 2004/0035208 A1 | 2/2004 | Diaz et al. | |
| 2004/0122443 A1 | 6/2004 | Berryman et al. | |
| 2004/0220527 A1* | 11/2004 | Buckley et al. | 604/191 |
| 2004/0236193 A1 | 11/2004 | Sharf | |
| 2004/0253185 A1 | 12/2004 | Herweck et al. | |
| 2004/0253281 A1 | 12/2004 | Herweck et al. | |
| 2005/0061198 A1 | 3/2005 | Khan et al. | |
| 2005/0100937 A1 | 5/2005 | Holmes | |
| 2005/0160817 A1 | 7/2005 | Clement et al. | |
| 2005/0172852 A1 | 8/2005 | Anderson et al. | |
| 2005/0234336 A1 | 10/2005 | Beckman et al. | |
| 2005/0251152 A1 | 11/2005 | Herweck et al. | |
| 2005/0258635 A1 | 11/2005 | Dominguez | |
| 2006/0095061 A1 | 5/2006 | Trautman et al. | |
| 2006/0108509 A1 | 5/2006 | Frangioni et al. | |
| 2006/0173362 A1 | 8/2006 | Toms et al. | |
| 2006/0228404 A1 | 10/2006 | Anderson et al. | |
| 2007/0027429 A1* | 2/2007 | Kuracina et al. | 604/116 |
| 2007/0032846 A1 | 2/2007 | Ferren et al. | |
| 2007/0106207 A1 | 5/2007 | Withey | |
| 2007/0162303 A1 | 7/2007 | Wiley, II et al. | |
| 2007/0192195 A1 | 8/2007 | Asmar et al. | |
| 2007/0203504 A1 | 8/2007 | Denny et al. | |
| 2007/0224252 A1 | 9/2007 | Trautman et al. | |
| 2007/0253614 A1 | 11/2007 | Jung et al. | |
| 2008/0009718 A1 | 1/2008 | Zohman | |
| 2008/0018429 A1 | 1/2008 | Kudoh et al. | |
| 2008/0125766 A1* | 5/2008 | Lubock et al. | 606/33 |
| 2008/0147038 A1* | 6/2008 | Hoffman | 604/500 |
| 2008/0161827 A1 | 7/2008 | Frost | |
| 2008/0208236 A1 | 8/2008 | Hobbs et al. | |
| 2008/0247637 A1 | 10/2008 | Gildenberg | |
| 2008/0257961 A1* | 10/2008 | Lubow | G06K 17/00 235/462.01 |
| 2008/0269596 A1 | 10/2008 | Revie et al. | |
| 2008/0287913 A1* | 11/2008 | Schwab | A61M 37/0069 604/518 |
| 2009/0018403 A1 | 1/2009 | Black et al. | |
| 2009/0039158 A1 | 2/2009 | Grishin et al. | |
| 2009/0076338 A1 | 3/2009 | Zdeblick et al. | |
| 2009/0110730 A1* | 4/2009 | Fritz | A01K 11/00 424/484 |
| 2009/0131479 A1 | 5/2009 | Palmer et al. | |
| 2009/0210165 A1 | 8/2009 | Christensen et al. | |
| 2010/0125028 A1 | 5/2010 | Heppert | |
| 2010/0211079 A1 | 8/2010 | Aramant | |
| 2010/0221188 A1 | 9/2010 | Clark et al. | |
| 2011/0275930 A1 | 11/2011 | Jho et al. | |
| 2011/0313288 A1 | 12/2011 | Chi Sing et al. | |
| 2012/0150023 A1 | 6/2012 | Kaspar et al. | |
| 2012/0215230 A1* | 8/2012 | Lubock et al. | 606/116 |
| 2012/0283637 A1* | 11/2012 | Cohen | 604/116 |
| 2013/0046182 A1 | 2/2013 | Hegg et al. | |
| 2013/0197447 A1* | 8/2013 | Smith | 604/191 |

OTHER PUBLICATIONS

Dubach et al.; "In vivo sodium concentration continuously monitored with fluorescent sensors"; Integrative Biology; 2011; pp. 142-148; Abstract; two pages; vol. 3.

Filonov et al.; "Bright and stable near-infrared fluorescent protein for in vivo imaging"; Nature Biotechnology; Aug. 2011; pp. 757-763 including two sheets of supplemental information; vol. 29, No. 8; Nature American, Inc.

George, Alexander; "Digital Tattoo Gets Under Your Skin to Monitor Blood"; pp. 1-22; last accessed on Aug. 9, 2011; located at http://www.wired.com/gadgetlab/tag/science.

Han et al.; "Quantum-dot-tagged microbeads for multiplexed optical coding of biomolecules"; Nature Biotechnology; Jul. 2001; pp. 631-635; vol. 19; Nature Publishing Group.

Holland et al.; "Intradermal Influenza Vaccine Administered Using a new Microinjection System Produces Superior Immunogenicity in Elderly Adults: A Randomized Controlled Trial"; The Journal of Infectious Diseases; Sep. 1, 2008; pp. 650-658.

Keck, Jr. et al.; "Aripiprazole Monotherapy for Maintenance Therapy in Bipolar I Disorder: A 100-Week, Double-Blind Study Versus Placebo"; J. Clin. Psychiatry; Oct. 2007; pp. 1480-1491; vol. 68, No. 10.

Kryszczuk et al.; "Singular point detection in fingerprints using quadrant change information"; 4 pgs.; located at portal.acm.org/citation.cfm?id=1172857, last visited on Jun. 8, 2011.

Larson et al.; "Water-Soluble Quantum Dots for Multiphoton Fluorescence Imaging in Vivo"; Science; May 30, 2003; pp. 1434-1436 including seven sheets of supplemental information attached; vol. 300; American Association for the Advancement of Science.

McAllister et al.; "Microfabricated needles for transdermal delivery of macromolecules and nanoparticles: Fabrication methods and transport studies"; PNAS; Nov. 25, 2003; pp. 13755-13760.

Merck & Co., Inc.; M-M-R® II (Measles, Mumps, and Rubella Virus Vaccine Live); Product Description; bearing a date of Dec. 2010; pp. 1-12.

Ocean Optics; "QE65000-FL Scientific-grade Spectrometer for Fluorescence Measurements"; pp. 1-4; last accessed on Apr. 26, 2011; located at http://www.oceanoptics.com/Products/qe65000FL.asp#Demanding.

Q Imaging; QImaging QIClick digial CCD Camera; data sheet; two pages; printed on Aug. 9, 2011; located at www.qimaging.com.

Saber et al.; "Partial shape recognition by sub-matrix matching for partial matching guided image labeling"; Pattern Recognition; 2005; pp. 1560-1573; vol. 38; Elsevier Ltd.

Shibata et al.; "Injectable hydrogel microbeads for fluorescence-based in vivo continuous glucose monitoring"; PNAS; Oct. 19, 2010; pp. 17894-17898 including five pages of supporting information attached; vol. 107, No. 42.

Belongie, Serge et al., "Shape Matching and Object Recognition Using Shape Contexts", IEEE Transactions on Pattern Analysis and Machine Intelligence, Apr. 2002, pp. 509-510, vol. 24, No. 24, IEEE.

(56) References Cited

OTHER PUBLICATIONS

Birdwell, Robyn L. et al., "Clip or Marker Migration 5-10 Weeks after Stereotactic 11-gauge Vacuum-assisted Breast Biopsy: Report of Two Cases[1]" Radiology, Nov. 2003, pp. 541-544, RSNA.

"Contrast Resolution", Wikipedia, located at http://en.wikipedia.org/wiki/Contrast_resolution, printed on Jun. 28, 2012, pp. 1-2.

Couture, O. et al., "Model for the ultrasound reflection from micro-beads and cells distributed in layers on a uniform surface", Phys Med Biol., Jul. 21, 2007, pp. 1-1, vol. 52, No. 14. (Abstract Only).

"Encoded microparticles for isolated cell and embryo tracking", located at http://www.uab.es/servlet/Satellite/serveis-a-empreses/oferta-tecnologica-1245651215252.html?param1-3021, printed on Jul. 27, 2012, Parc de Recerca UAB.

Gattiker, F. et al., "Novel ultrasound read-out for a wireless implantable passive strain sensor (WIPSS)", Sensors and Actuators, 2008, pp. 291-298, vol. A 145-146, Elsevier B.V.

Ho, Yi-Ping et al., "Multiplexed Hybridization Detection with Multicolor Colocalization of Quantum Dot Nanoprobes", Nano Letters, 2005, pp. 1693-1697, vol. 5, No. 9, American Chemical Society.

"Markers for predictable placement and rapid expansion", Mammotome, located at http://www.mammotome.com/Mammotome/Products/Tissue-Markers/index.htm, printed on Aug. 30, 2012, pp. 1-2, Devicor Medical Products, Inc.

Murray, Charles J., "Injectable Chip Opens the Door to 'Human Bar Code'", EETimes.com, located at http://resnse.com/general18/injectable.htm, printed on Jul. 27, 2012, pp. 1-6.

Serago, Christopher F. et al., "Comparison of Daily Megavoltage Electronic Portal Imaging or Kilovoltage Imaging with Marker Seeds to Ultrasound Imaging or Skin Marks for Prostate Localization and Treatment Positioning in Patients with Prostate Cancer", Int. J. Radiation Oncology Biol. Phys, 2006, pp. 1585-1592, vol. 65, No. 5, Elsevier Inc.

Stern, Roger A. et al., "A Biologically Compatible Implantable Ultrasonic Marker", Ultrasound in Medicine & Biology, 1983, pp. 191-199, vol. 9, No. 2, Pergamon Press Ltd.

Stoll, Jeffrey et al., "Passive Markers for Ultrasound Tracking of Surgical Instruments", MICCAI 2005, LNCS 3750, 2005, pp. 41-48, Springer-Verlag Berlin Heidelberg.

"Tissue Markers"; Mammotome, a division of Devicor Medical Products, Inc.; 2 pages; May 17, 2011; located at htttps://web.archive.org/web/20110517031051 /http://www.mammotome.com/Mammotome/Products/Tissue-Markers.

Tomasi, Carlo, "Computer Vision", CPS 274 Lecture Notes—Duke University, Fall 2009.

"UltraClip® Dual Trigger Breast Tissue Marker", located at http://www.bardbiopsy.com/products/ultraclip_dual.php, printed on Aug. 20, 2012, C. R. Bard, Inc.

* cited by examiner

FIG. 1
M T W Th Fr Sa Su
 Green Dots (propranolol)
 Brown Ovals (hydrochlorothiazide)

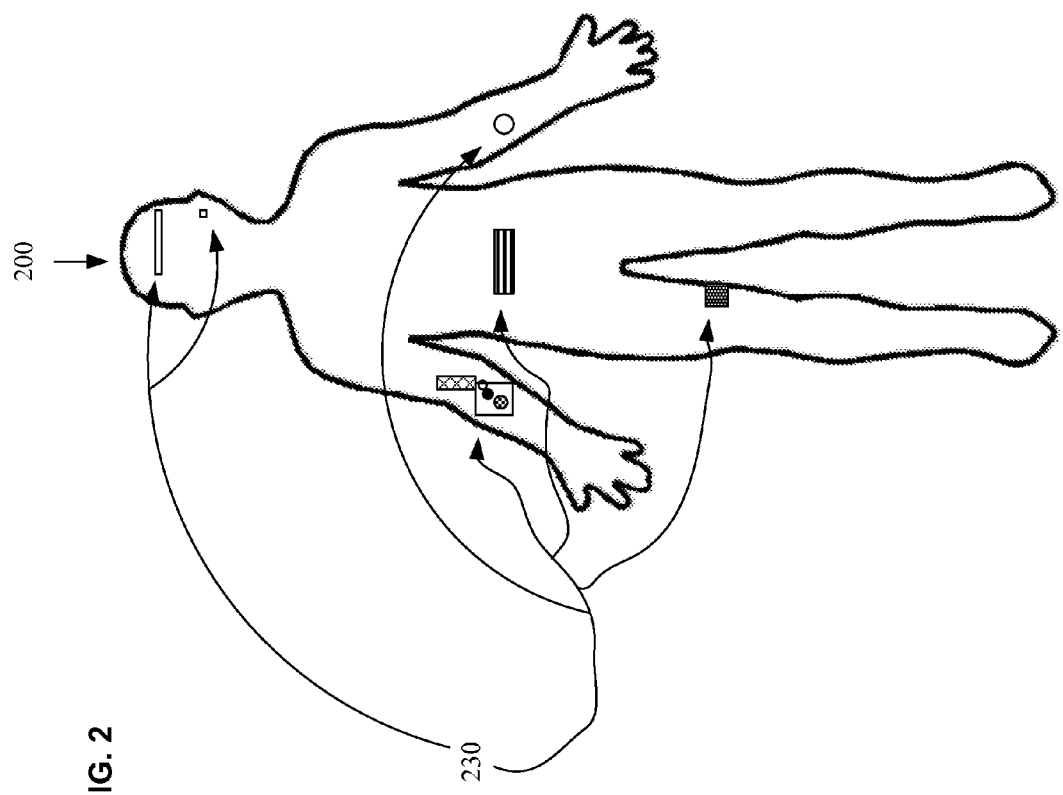
FIG. 2
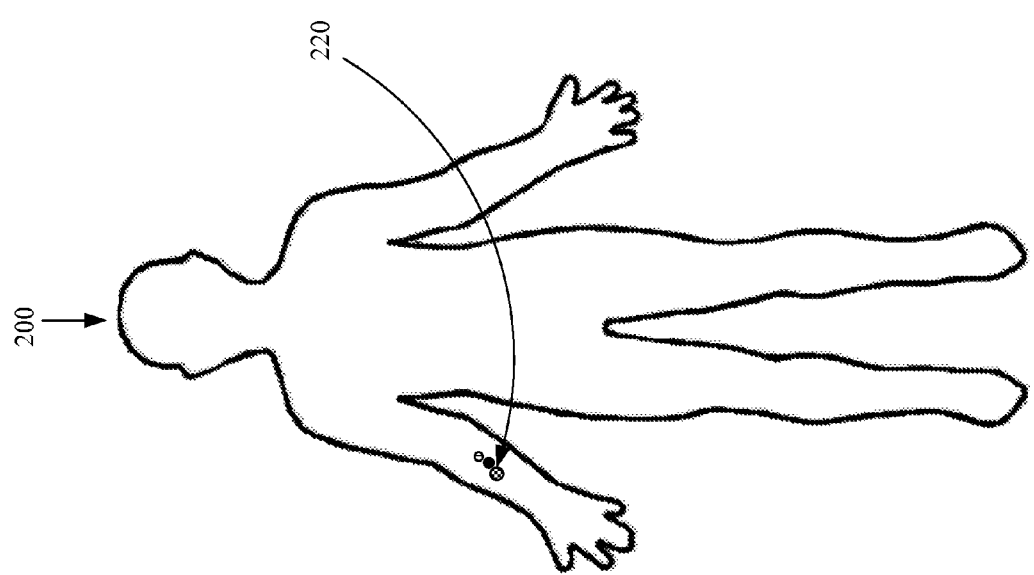

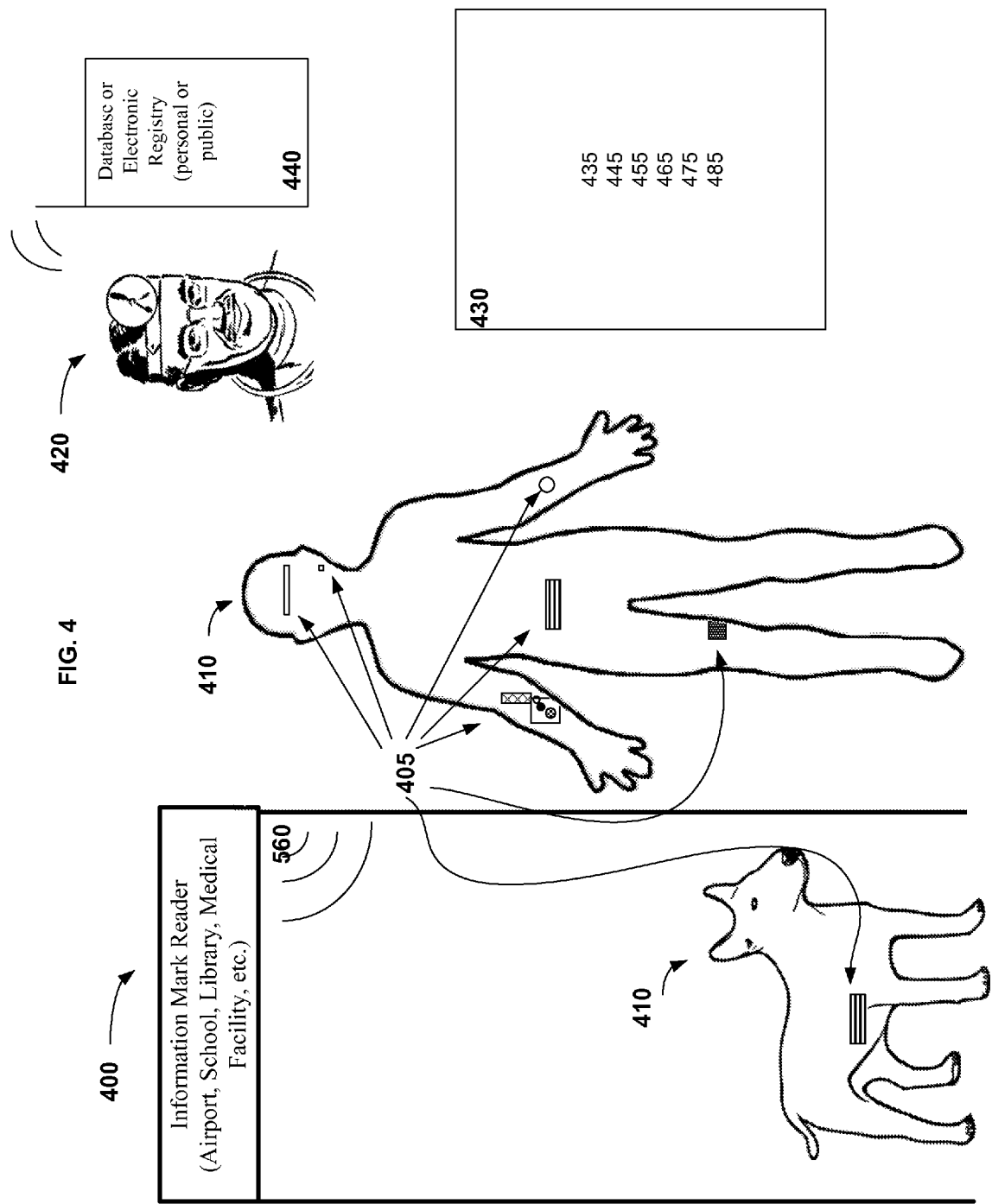

DEVICES AND METHODS FOR RECORDING INFORMATION ON A SUBJECT'S BODY

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications, including any priority claims, is incorporated herein by reference to the extent such subject matter is not inconsistent herewith.

RELATED APPLICATIONS

For purposes of the USPTO extra-statutory requirements, the present application constitutes a continuation-in-part of U.S. patent application Ser. No. 13/199,038, entitled DEVICES AND METHODS FOR RECORDING INFORMATION ON A SUBJECT'S BODY, naming Roderick A. Hyde, Jordin T. Kare, Wayne R. Kindsvogel, Royce A. Levien, Erez Lieberman, Mark A. Malamud, Nathan P. Myhrvold, Elizabeth A. Sweeney, Clarence T. Tegreene, Charles Whitmer and Lowell L. Wood, Jr. as inventors, filed 16 Aug. 2011, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 13/199,047, entitled DEVICES AND METHODS FOR RECORDING INFORMATION ON A SUBJECT'S BODY, naming Roderick A. Hyde, Jordin T. Kare, Wayne R. Kindsvogel, Royce A. Levien, Erez Lieberman, Mark A. Malamud, Nathan P. Myhrvold, Elizabeth A. Sweeney, Clarence T. Tegreene, Charles Whitmer and Lowell L. Wood, Jr. as inventors, filed 16 Aug. 2011, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, Benefit of Prior-Filed Application, USPTO Official Gazette Mar. 18, 2003. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above, but expressly points out that such designation(s) are not to be construed in any way as any type of commentary and/or admission as to whether or not the present application contains any new matter in addition to the matter of its parent application(s).

SUMMARY

Various embodiments are disclosed herein that relate to methods, devices, systems, and computer program products for providing at least one information mark to a subject in conjunction with administration of at least one medical treatment to the subject. In an embodiment, the at least one information mark represents information regarding the at least one medical treatment, and optionally entitlement of the recipient subject to at least one reward based on the administration of the at least one medical treatment. In an embodiment, a method includes providing at least one information mark to a subject in conjunction with administration of at least one therapeutic agent to the subject. In an embodiment, the at least one information mark represents information regarding the at least one therapeutic agent, and entitlement of the recipient subject to at least one reward based on the administration of the at least one therapeutic agent. In an embodiment, a method provides at least one reward for receipt by a subject of a medical treatment, including monitoring the subject for administration of a medical treatment by the subject or another entity, generating information relating to the medical treatment of the subject, transmitting at least some information relating to the medical treatment; and providing an entitlement to the recipient subject of at least one reward.

In an embodiment, devices, computer systems, computer program products, and computer-implemented methods assist or provide for administration of at least one information mark to a subject in conjunction with administration of at least one medical treatment.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 1 illustrates a partial view of a particular embodiment described herein.

FIG. 2 illustrates a partial view of a particular embodiment described herein.

FIG. 4 illustrates a partial view of a particular embodiment described herein.

DETAILED DESCRIPTION

Figure 3:
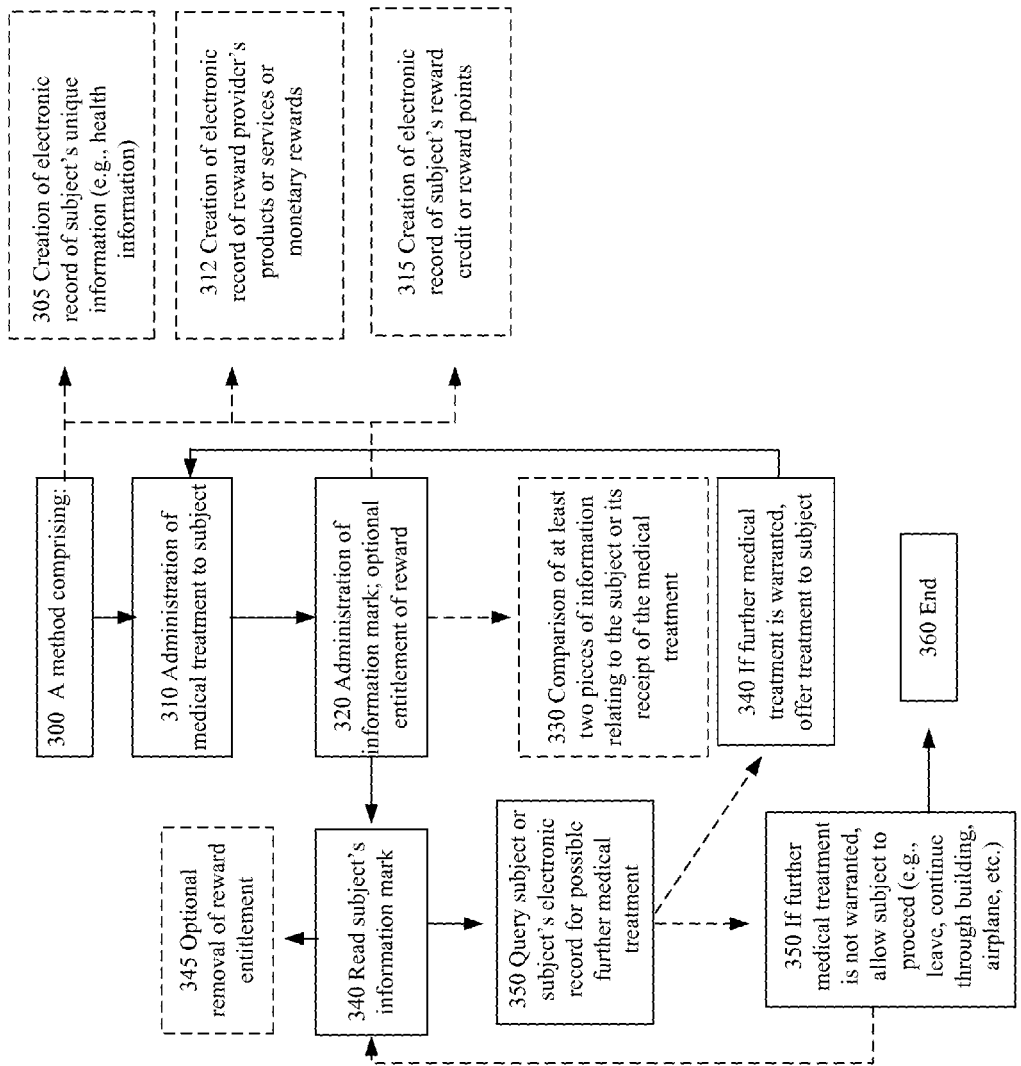
FIG. 3 illustrates a partial view of a particular embodiment described herein.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

In an embodiment, at least one of the methods, devices, or computer systems disclosed herein are utilized for documenting information regarding a subject's health, including but not limited to vaccination history, or health status. In an embodiment, a device (e.g., an injector) is configured to administer an information mark (e.g., including information relating to administration of at least one medical treatment (including medical intervention such as diagnosis, prognosis, prevention, etc.), including but not limited to administration of at least one therapeutic agent (e.g., vaccination or other agent); information relating to prescribed therapeutic agents; information relating to passwords for the subject's implantable medical devices or other related medical devices; information relating to a subject's weight or height; information relating to a subject's medical history including allergies, genetic predisposition(s) to particular diseases or disorders, mental health history or behavioral tendencies, use of alcohol, tobacco, or other drugs, number of offspring, pregnancies, fertility or ovulation cycle; information relating to a subject's history of drug treatment or mental health treatment; information relating to a subject's insurance carrier or other third party payor; or other information on a subject in a visible or non-visible manner. In an embodiment, the information mark includes at least one piece of information that is unique to the subject to whom it is administered. That is, in certain aspects, the information marks are able to be customized to the subject who is receiving the particular medical treatment. Information relating to administration of a therapeutic agent includes, but is not limited to, the type of therapeutic agent, dosage, date, administrator, manufacturer, lot, location site of clinic, medical history, allergies, laboratory test results, next suggested dose, etc. In an embodiment, at least one information mark relates to a future administration of a medical treatment (e.g., surgery).

In an embodiment, a subject includes, but is not limited to, a human or non-human animal (for example, pet, livestock, food animals, wild animals, game animals, etc.).

In an embodiment, the information is provided by a magnetic, reflective, fluorescent, acoustic-scattering (e.g., ultrasonic scattering), luminescent, radioactive, conductive, or other marker that provides a measurable characteristic for "reading" the information contained within the information mark or is represented by the information mark (e.g., by emitting one or more signals, or by providing non-emitting data). In an embodiment, at least one parcel of information relating to the information mark is coded or encrypted. In an embodiment, the information mark includes information that can interact with or be linked to an electronic personal health record. Some non-limiting examples of magnetic ink are disclosed in U.S. Pat. No. 7,344,587, which is incorporated herein by reference.

In an embodiment, the fluorescent marker includes, but is not limited by, phytochrome-based near-infrared fluorescent protein (iRFP), as described for example, in *Nature Biotech.* vol. 29, no. 8, pp. 757-763, which is incorporated herein by reference.

In an embodiment, the information mark can be further manipulated (e.g., "erased," encoded, re-coded, etc.). In an embodiment, the information mark can expire or become "unreadable" after a given time period. In an embodiment, the information mark can be set to not be "readable" immediately, but emit a signal once a time period has passed (e.g., to alert of the need for further dosing of a therapeutic agent). For example, in an embodiment, a given time period includes at least about one hour, at least about two hours, at least about three hours, at least about four hours, at least about five hours, at least about a day, at least about two days, at least about three days, at least about four days, at least about five days, at least about one week, at least about two weeks, at least about three weeks, at least about four weeks, at least about five weeks, at least about one month, or more.

In an embodiment, the information mark includes a marking visible or invisible to the naked eye. In an embodiment, the information mark can be "read" via reflection at specific wavelength(s) (e.g., infrared, visible, ultraviolet, etc.). In an embodiment, the information mark can be "read" via fluorescence (e.g., quantum dots). In an embodiment, the information mark is magnetic or conductive and is "readable" by electronic or magnetic devices. In an embodiment, the information mark is administered to a subject with or without the subject's knowledge. In an embodiment, the device configured to administer the information mark to a subject includes at least one of a needle, inhaler, transdermal patch, microneedle, needle array, inkjet, needle-less injection (including but not limited to microprotrusions, microneedles, cannula, microcannula, polymer microneedles), etc. In an embodiment, needle-less injection can include metal, biodegradable, hollow, solid, etc. and other formations or formulations. For example, hollow protrusions can include a trough, which provides capillary motion and coating via this capillary motion or jet propulsion. See for example, U.S. Pat. Pub. No. 2007/0224252, which is incorporated herein by reference. In an embodiment, a needle leaves a hidden notation designating it was used (e.g., dispensing of X-Ray Fluorescent-readable material).

In an embodiment, the at least one information mark indicates a specific medical treatment (e.g., chemotherapy, stem cell transplant, etc.) has been administered to a subject.

In an embodiment, the at least one information mark includes at least one of magnetic ink, RFID ink (e.g., Somark's), LED, silk silicon implant, or quantum dot(s).

In an embodiment, a receiver is configured for receiving an information signal from the information mark. In an embodiment, the receiver optionally forwards at least some of the information from the information mark to a database (e.g., computer system), where the information can be stored (e.g., in a database). In an embodiment, the computer system including the database also includes one or more input/output devices to provide for entry of inputs by a user or for the presentation of information to the user. Various types of input/output devices are known, including for example, audio, visual, electronic, tactile, or other forms (e.g., scanner, touchscreen, keyboard, mouse, trackball, button, dial, microphone, speaker, video display, etc.). In an embodiment, the computer system includes a controller, which can be one or more of hardware, software, or firmware. In an embodiment, the controller includes a microprocessor. In an embodiment, the computer system includes an imaging device (e.g., CCD camera, or sensor system, etc.).

In an embodiment, a comparator (e.g., as part of the computer system), is configured to compare at least two parcels of information relating to the subject. For example, the comparator can be configured to compare a type, quantity, or timing of a therapeutic agent received by the subject (e.g., vaccination), with the type, quantity, or timing of the therapeutic agent prescribed by a physician or other health care provider. For example, comparator software modules are known. See, for example, U.S. Patent App. Pub. No. 2002/0087437, which is incorporated herein by reference.

In an example, the comparator can be configured to compare a type, quantity, or timing of a therapeutic agent prescribed by the subject with a type, quantity, or timing of a therapeutic agent available at the healthcare facility or in a pharmacy warehouse. In another example, the comparator can be configured to compare a type, quantity, or timing of a therapeutic agent taken at present by the subject, or taken in the past (e.g., by linking with the subject's electronic health record). In another example, the comparator can be configured to compare a type, quantity, or timing of a therapeutic agent prescribed for the subject, with any known allergies of the subject (e.g., by linking with the subject's electronic health record).

In an embodiment, an information signal from the information mark is automatically linked to an electronic health record, or automatically creates an electronic health record, and is optionally automatically entered into a database of other information about the subject or (an)other subject(s). For example, in an embodiment, an electronic health record includes a population database. In an embodiment, the population database includes information submitted anonymously. In an embodiment, the population database includes information submitted with identifying information such that an individual subject is identifiable. In an embodiment, the population database includes at least some information submitted anonymously and at least some information submitted with identifying information. In an embodiment, the population database includes at least one protocol or computer algorithm to avoid submission of the same information twice.

In an embodiment, the device configured to administer the information mark is also capable of "reading" the same and/or other information marks. In an embodiment, the information mark is read by the subject itself. In an embodiment, the information mark is read by a second or third party. In an embodiment, the information mark is read by another party in order to ensure compliance, reward, insurance coverage, public health assessment, or other instances.

In an embodiment, upon receiving an information mark, the subject is entitled to at least one reward. The reward can include, but is not limited to, for example, monetary rewards, or discounted or free products or services. In an embodiment, the subject receives an information mark including information relating to entitlement of at least one reward. In an embodiment, receipt of several information marks enable the subject to be eligible for increasingly beneficial rewards (for example, each additional mark increases the discount on the product or service until enough information marks have been administered to earn the subject a free product or service). In an embodiment, at least one reward includes a "credit" with a health insurance company, or third party medical expense payor. In an embodiment, the subject is included in a cohort of other subjects—some of which are receiving a therapeutic agent (e.g., vaccination), and some of which are not (e.g., refusal of vaccination or non-compliance with medical prescriptions, etc.) and those subjects that are receiving a therapeutic agent receive information marks that entitle them to at least one reward, while the subjects that are not receiving a therapeutic agent do not receive the information mark, and are not entitled to the same reward.

In an embodiment, an information mark allows the subject a selection of possible rewards. In an embodiment, receipt of multiple information marks allows the subject a broader selection of possible rewards. In an embodiment, receipt of multiple information marks allows the subject a greater selection of higher value rewards (e.g., more valuable products or services, or greater discount on a product or service). In an embodiment, one or more information marks from one subject include information that is electronically linked to one or more information marks from at least one other subject.

For example, a first family member receives a vaccination, and a corresponding information mark. A second family member receives a vaccination, and at least some of the information from his or her information mark is electronically linked to the first family member's information mark in an electronic registry (e.g., a computer database) for purposes of identification, convenience, third party payor purposes, etc., and can optionally enable the first and second family members to receive entitlement to higher value rewards due to compliance of multiple family members. In an embodiment, at least some of the information of at least one information mark is capable of being electronically linked to an electronic health record. Such an electronic health record can be shared with, for example, other family members, or a third party payor. In an embodiment, electronically linking the information from an information mark to an electronic health record enables the subject to receive entitlement to a higher value reward, or a greater selection of rewards.

In an embodiment, a method for rewarding receipt by a subject of a medical treatment (e.g., receiving at least one therapeutic agent) includes at least one of monitoring the subject for administration by the subject or another individual, of a medical treatment to the subject, generating information relating to the medical treatment of the subject, transmitting or transferring at least some information relating to the medical treatment (e.g., administration of at least one therapeutic agent) to a subject by way of a computing system (e.g., computer, internet, processor, etc.), and optionally converting at least some of the information relating to the medical treatment into reward points for the subject. In an embodiment, the receipt by the subject of a medical treatment is monitored, and information relating to entitlement of reward for the subject is based on successful receipt of a medical treatment.

In an embodiment, the computing system includes, for example, at least one of a notebook computer, a personal data device, a desktop computer, a cluster of processors, a cluster of servers, a cloud computing center, a mobile telephone, or other computing device.

In an embodiment, a computer or other processing unit is configured to receive or transmit information relating to receipt of a therapeutic agent by a subject by, for example, a USB cable or wireless network. In an embodiment, a computer or other processing unit is configured for receiving or storing information. In an embodiment, a computer or other processing unit is configured to allocate or regulate establishment or usage of reward points, or reward redemption. See, for example, U.S. Pat. No. 6,980,670, which is incorporated herein by reference.

In an embodiment, the computer or other processing unit is configured to allow input of additional reward points, or information relating to administration of a medical treatment (e.g., therapeutic agent), for example, as in an account. In an embodiment, the account is an individual account. In an embodiment, the account is a group account. In an embodiment, an administrator or other participating subject can input information or reward points into a particular account based on receipt of a therapeutic agent by the subject. In an embodiment, a computer or other processing unit displays at least some information relating to receipt of a therapeutic agent to a subject. In an embodiment, at least some information relating to receipt of a medical treatment (e.g., therapeutic agent) by a subject is graphically displayed to an entity (e.g., human or computer). See, for example, U.S. Patent App. Pub. No. 2010/0125028, which is incorporated herein by reference.

In an embodiment, at least one information mark is readable by a device (e.g., handheld wand, portable device, wall mounted unit, doorway detector, etc.) at a hospital, clinic, other healthcare facility, or other public institution (school, airport, library, etc.). In an embodiment, if the subject passes by an information mark reader, the subject can have the option of receiving a medical treatment (e.g., therapeutic agent) at that time (e.g., vaccine "booster," or other therapeutic agent). In an embodiment, the subject can be required to receive a medical treatment (e.g. therapeutic agent) in order to proceed (exit the building or other space, continue to enter the building or other space (e.g., library, school, airport, etc.)), such as, for example, during a state of emergency or public health threat.

For example, the information mark reader can include, but is not limited to, a cell phone device, other handheld device, other portable device, a device built into a structure (for example, as part of a vehicle or doorway, etc.). In an embodiment, the information mark reader includes a camera, for example a camera/LED/filter as described in U.S. Patent App. Pub. No. 2010/0221188, and Integr. Biol. 3, pp. 142-148 (2011); each of which is incorporated herein by reference.

In an embodiment, a comparator is configured to compare at least two parcels of information from a subject's information mark(s) with each other, or compare at least one parcel of information from a subject's information mark to at least one parcel of information in an electronic registry (e.g., database). In an embodiment, a comparator is configured to determine if additional medical treatment is warranted. In an embodiment, a comparator is configured to determine what additional medical treatment is warranted.

In an embodiment, at least one information mark indicates the subject has health information stored in one or more electronic registry (e.g., electronic health records). In an embodiment, at least some of the information from one or more information marks is electronically linked to at least some other information from one or more electronic health record.

In an embodiment, a device (optionally linked to a computer system, including but not limited to a personal computer or personal data device) is configured to receive (and optionally interpret) at least some of the information included in the at least one information mark of the subject. In an embodiment, the device is further configured to gather or receive at least some information from an electronic health record. In an embodiment, a device or computer system configured to receive (and optionally interpret, or "read" the information contained in the information mark) at least some of the information represented by the at least one information mark of the subject, further is configured to make a determination (e.g., course of treatment, vaccine selection, dosage of therapeutic agent, potential allergy or drug interaction or incompatibility, etc.) based on at least some of the information of the subject's electronic health record. In an embodiment, the device configured to receive at least some of the information of the information mark is further configured to transmit at least some of the information to an electronic registry (e.g., database or electronic record).

In an embodiment, the information mark is human or non-human readable. In an embodiment, the information mark includes at least one representation (e.g., shape, animal, number, letter, or other symbol) that signifies at least one parcel of information, or single fact relating to the subject or subject's treatment. In an embodiment, the material(s) utilized to construct the information mark include, for example quantum dots, luminex dots, etc.

For example, non-human readable information marks include information marks that are machine readable, and can be in a form, for example, that can be read, captured, scanned, sensed, or imaged by a machine (e.g., computer), and optionally interpreted by the machine's hardware or software system. Non-limiting examples of information marks including non-human readable components include one-, two-, or multi-dimensional symbologies, stacked symbologies, fixed-length symbologies, multiple-width symbologies, variable-length symbologies, discrete symbologies, continuous symbologies, etc. Some specific examples include, but are not limited to: APOSTAL, CODE 128, CODE 39, CODE 49, CODE 93, CODE 931, CODE ONE, CODEABAR, DATA MATRIX, MAXICODE, PDF417, CODABAR, CODE 25, CODE 39, FULLASCII, CODE 39 HIBC, CODE 11, EAN-13, EAN-8, EAN supplements, ISBN/BOOKLAND, ITF25, MSI/PLESSEY, POSTNET, UCC/EAN-128, UPC/EAN, UPC-A, UPC-E, UPC supplements, and the like. Further discussion and examples of non-human readable symbols can be found, for example, in U.S. Pat. No. 7,546,955, which is incorporated herein by reference.

In other examples, human readable information marks can include, for example, alphabets (e.g., English, Japanese, Cyrillic, Greek, Hebrew, Chinese, Kanji, Arabic, Farsi, French, German, Latin, Italian, Spanish, etc.). Other examples of human readable information mark symbols include, but are not limited by, optical character recognition fonts, OCR-A, OCR-B, OCRA I, OCRA III, OCRA IV, OCRB I, OCRB III, and OCRB IV, etc. Other specific non-limiting examples can be found, for example, in U.S. Pat. No. 7,546,955, Ibid.

In an embodiment, as can be seen in the Figures, the at least one information mark and the at least one therapeutic agent have different spatial locations on the subject's body. In an embodiment, the at least one information mark and the at least one therapeutic agent have different temporal locations on the subject's body.

In an embodiment, the material(s) utilized to construct the information mark include a spatial or temporal pattern or other representation that signifies certain information. For example, measuring certain biometric characteristics of a subject can be utilized as unique identifiers (e.g., fingerprints, iris scan, retinal scan, etc.). For example, computer algorithms have been developed for ease of measuring points and patterns of such biometric characteristics. See, for example, "Singular Point Detection in Fingerprints Using Quadrant Change Information," Kryszczuk and Drygajlo, on the world wide web at: portal.acm.org/citation.cfm?id=1172857, last visited on Jun. 8, 2011, the content of which is incorporated herein by reference. Furthermore, partial shape recognition algorithms have been developed that are translation, rotation, scale, and reflection invariant. See, for example, "Partial Shape Recognition by Sub-matrix Matching for Partial Matching Guided Image Labeling," Saber, et al., Pattern Recogn. pp. 1560-1573 (2005).

Thus, in an embodiment, by determining one or more specific spatial or temporal pattern(s) desired, a pre-determined spatial or temporal pattern is designed as a unique identifier for a particular subject, corresponding to at least one unique attribute of that subject including but not limited to height, weight, genomic or proteomic profile, genetic information, social security number, random assigned identifier, familial relationship(s), medical treatment, receipt of at least one therapeutic agent, predicted medical treatment, or other identifier. For example, as a temporal pattern is constructed over time (e.g., receiving multiple vaccinations of the same or different type), each step of constructing the pattern, or the completed pattern, or various stages of completion can entitle the subject to one or more rewards. In an embodiment, as the pattern is constructed, the value or frequency of the reward is increased. In an embodiment, multiple layers of complexity are built into the pattern, so that a first portion completed is able to trigger a special reward once a second portion is completed. In an embodiment, completion of at least one portion allows the subject to move on to a second level of complexity of the pattern, and begin to complete a second portion of the pattern. In an embodiment, a device is configured to read multiple information marks, optionally including spatial or temporal patterns.

In an embodiment, at least some of the information included in the spatial or temporal pattern is electronically linked to an electronic registry (e.g., electronic health record). In an embodiment, the electronic health record is only for the subject receiving the medical treatment. In an embodiment, the electronic health record includes at least part of a cohort of subjects.

In an embodiment, at least one information mark is included in a therapeutic agent (e.g., in solution, in suspension, in simultaneous administration delivery mechanism, etc.), such that the information mark is administered to the subject simultaneously with the therapeutic agent.

In an embodiment, a device configured for administering the at least one information mark, or for "reading" an information mark, is further configured for accessing information from one or more electronic sources (e.g., world wide web, database, etc.) and incorporating it into the information mark, or interpreting the information mark in light of the accessed information. For example, the device can include a transmitter, transceiver, receiver, or other component that is configured to send or receive information from one or more electronic sources.

In an embodiment, a system includes collecting and optionally maintaining data in a database regarding medication compliance (e.g., computer and optional computer network). In an embodiment, the system collects at least some information from a detector or reader set up in a public area, for example a public walkway (e.g., airport, school, etc.) or a public waiting area or a public vehicle (e.g., an airplane, train, or bus). In an embodiment, the subject is unaware that his or her information mark(s) have been scanned or read.

In an embodiment, authorization to access or read an information mark on a subject is provided for various entities (e.g., school administrators, law enforcement officials, health care providers, public health officials, the military, etc.), and each entity can access information included in an information mark of a subject according to that particular entity's authorization level. In an embodiment, a device or computer system described herein further comprises means for collecting personal information relating to the subject that is not included in the at least one information mark. For example, the means for collecting personal information includes, but is not limited to, circuitry configured for collecting personal information. In an embodiment, a method includes collecting personal information relating to the subject that is not included in the at least one information mark.

In an embodiment, a device or computer system described herein further comprises means for comparing information included in the at least one information mark with the personal information collected. For example, the means for comparing information includes, but is not limited to, circuitry configured for comparing information. In an embodiment, a method includes comparing information included in the at least one information mark with the personal information collected.

In an embodiment, a device or computer system described further comprises means for transmitting the personal information relating to the subject to at least one electronic registry. In an embodiment, means for transmitting the personal information relating to the subject to at least one electronic registry includes, but is not limited to, circuitry configured for transmitting the personal information relating to the subject to at least one electronic registry. In an embodiment, the computer system or device includes a wireless transmitter. In an embodiment, the computer system or device includes a wired transmitter. In an embodiment, a method described herein further comprises transmitting the personal information relating to the subject to at least one electronic registry.

In an embodiment, a computer system or device described herein further comprises means for selecting authorization to access or read information included in the at least one information mark of the subject. In an embodiment, the means for selecting authorization to access or read information included in the at least one information mark of the subject includes, but is not limited to, circuitry configured for selecting authorization to access or read information included in the at least one information mark of the subject. In an embodiment, a method described herein further comprises selecting authorization to access or read information included in the at least one information mark of the subject.

In an embodiment, any method described herein is a computer-implemented method.

In an embodiment, a database that records, compares, or otherwise is linked to, interacts with, or is utilized with an information mark is configured to be queried, searched, allow for comparison or analysis of data, allow for filtering, sorting, editing, or otherwise manipulating by a user. In an embodiment, the user is a human. In an embodiment, the user is a computer or computer system (including a software module, for example).

In an embodiment, a first electronic registry (including but not limited to an electronic health record) is created. In an embodiment, the first electronic registry includes, but is not limited to, personal health information. In an embodiment, a second electronic registry (as part of the first electronic registry, or separate therefrom) is created. In an embodiment, the second electronic registry includes, but is not limited to, a reward provider's products or services. In an embodiment, a third electronic registry (as part of the first or second electronic registries, or separate therefrom either or both) is created. In an embodiment, the third electronic registry includes, but is not limited to, the subject's reward credit or reward points.

In an embodiment, at least a portion of the information mark of a subject is configured to be removed by the subject's body (e.g., biodegradation, bioabsorption, etc.). In an embodiment, at least a portion of the information mark of a subject is configured to be removed only through assistance (e.g., chemical treatment, mechanical treatment, chemo-mechanical treatment, pressure, electromagnetic field, surgery, etc.).

As shown in FIG. 1, as described elsewhere herein, in an embodiment, to monitor adherence to a treatment plan, a patient is injected in the skin of the wrist with magnetic microparticles containing chromophores, and an inert polymer coating. Magnetic microparticles composed of $Fe_3O_4$, approximately 1 μm in diameter are available from Bangs Laboratories Inc., Fishers, Ind. The magnetic microparticles are coated with chromophores (e.g., FD&C Blue No. 1 and FD&C Red No. 3), to create blue and red magnetic particles, respectively. A transparent, inert, biocompatible coating is applied to protect the particles (e.g., Epo-Tek®301 available from Epoxy Technology, Billerica, Mass.), and the particles are suspended in a carrier such as 20% (w/w) glycerin. The particles may also be non-magnetic, and colored with a chromophore (e.g., FD&C Yellow No. 6), to create yellow particles that are not influenced by a magnetic field. Methods and compositions for creating magnetic tissue markings are described (see e.g., U.S. Pat. No. 7,344,587, which is incorporated herein by reference).

A pattern of colored magnetic markings is injected on the wrist immediately beneath the epidermis of the patient (approximately 100 μm to 300 μm beneath the skin). An oscillating tattoo machine with a needle array may be used to inject the particles (e.g., Spaulding Tattoo Machine available from Spaulding and Rogers, Albany, N.Y.), and create a pattern that encodes dosing information.

A pattern of colored magnetic and nonmagnetic particles is implanted under the patient's epidermis to monitor treatment with multiple drugs. To indicate twice daily dosing with 80 mg of propranolol, two rows of dots (with 7 dots per row) are injected using a mix of magnetic blue particles and nonmagnetic yellow particles, to create green dots. To indicate daily dosing with 15 mg of hydrochlorothiazide, one row of 7 ovals is injected using a mix of magnetic red particles and non-magnetic yellow particles, to create brown ovals. The pattern of magnetic to non-magnetic particles itself can be "read" as containing information, or representing information.

As shown in FIG. 2, a subject 200, has received a single information mark 220, or a series of information marks 230 that become part of a larger pattern of representation when the subject 200 receives additional information marks as a result of further medical treatment. Thus, in an embodiment, additional information is included in the additional information marks, as well as in the pattern as a whole, resulting in a combinatorial increase in representation of information by the information marks.

As depicted in FIG. 3, in an embodiment, a method 300 includes administration 310 of medical treatment (e.g., at least one therapeutic agent) to a subject; administration 320 of an information mark and optional entitlement of reward; optional comparison 330 of at least two parcels of information relating to the subject or its receipt of the therapeutic agent or other medical treatment; and a decision that 340 if further medical treatment is warranted, then treatment is offered to the subject. In an embodiment, following administration 320 of an information mark and optional entitlement of reward, the subject's information mark can be read 340. In an embodiment, subsequent to "reading" the subject's information mark, the subject or subject's electronic record can be queried 350 for possible further medical treatment, and optionally, if further medical treatment is not warranted 350, then the subject is allowed to proceed (e.g., leave, continue through the building, airplane, etc.), and optionally return to read the subject's information mark again 340. Optionally, in an embodiment, a reward entitlement may be removed 345. Optionally, in an embodiment, creation 305 of an electronic record of subject's unique information (e.g., health information) can occur prior to administration of medical treatment to a subject, during administration of medical treatment to a subject, or subsequent to administration of medical treatment to a subject. Optionally, in an embodiment, creation 312 of an electronic record of a reward provider's products or services, or other monetary rewards can occur prior to administration of medical treatment to a subject, during administration of medical treatment to a subject, or subsequent to administration of medical treatment to a subject. Optionally, in an embodiment, creation 315 of electronic record of a subject's reward credit or reward points can occur prior to administration of medical treatment to a subject, during administration of medical treatment, or subsequent to administration of medical treatment to a subject. Once the entire method has been executed, with no additional or optional loops, the method ends 360.

As shown in FIG. 4, a subject 410 who has received at least one information mark 405, passes near or through an information mark reader 400 (located, for example, at an airport, school, library, medical facility, etc.) and at least some of the information is read. In an embodiment, the information mark reader 400 (e.g., camera, fluorescent receiver, etc.) is operably coupled with a device configured to administer at least one information mark, and/or at least one therapeutic agent. In an embodiment, at least one of the following method steps 430 occurs (automatically, or manually entered by a user): administration 435 of an information mark; recordation 445 of at least some information of an information mark (e.g., at least one parcel of information); transmission 455 of at least some information of an information mark (e.g., at least one parcel of information); storage 465 of at least some information of an information mark; comparison 475 of at least some information of an information mark; or query 485 of database or electronic record of the subject (or public electronic registry) 440. In an embodiment, a health care professional 420 locally or remotely receives information related to the information mark(s) of the subject and optionally offers additional medical treatment (e.g., vaccination) if it is deemed to be warranted. If no further medical treatment is deemed to be warranted, the subject is allowed to proceed. In an embodiment, the information mark reader 400 includes at least one receiver 560.

Figure 5A:
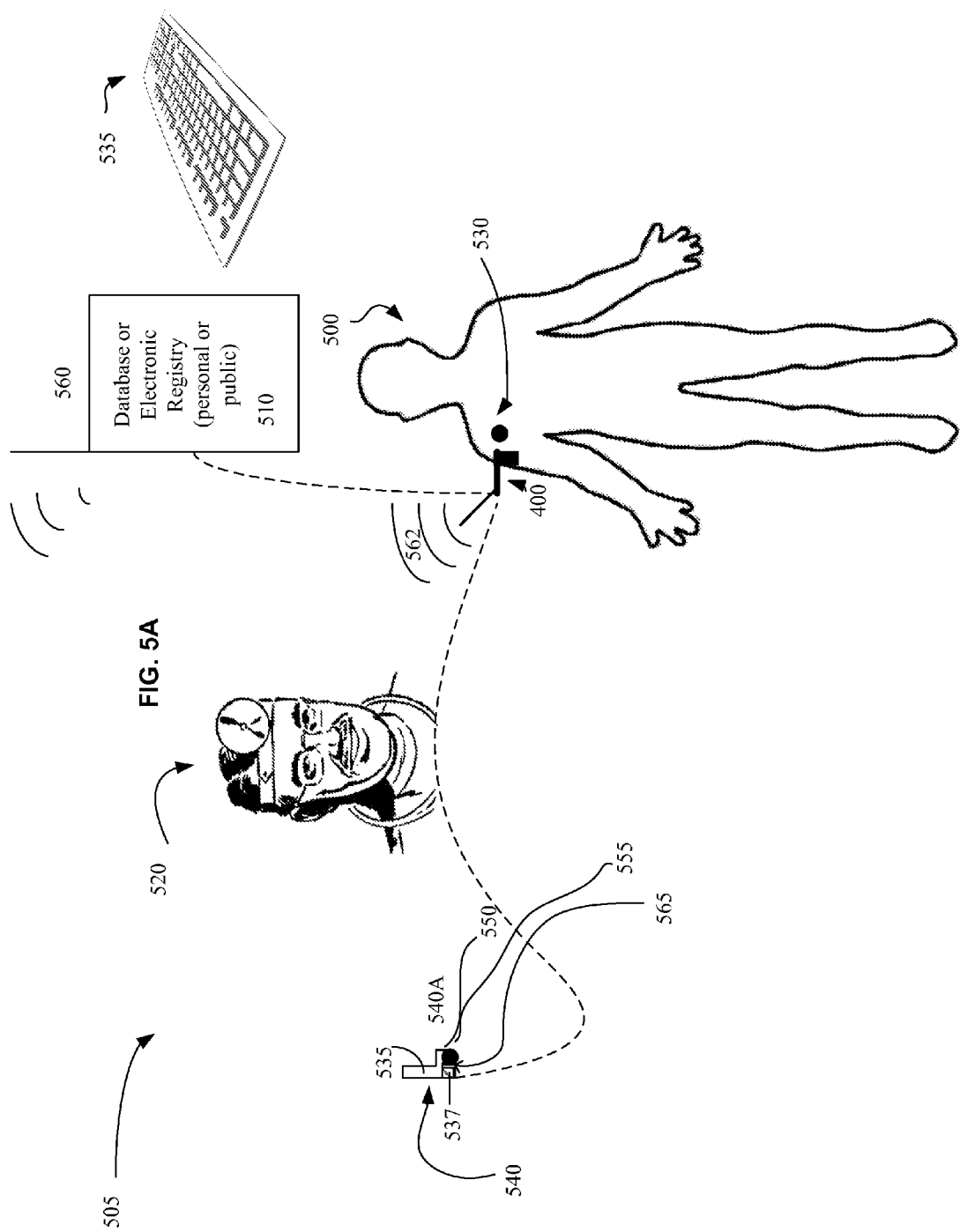
FIG. 5A illustrates a partial view of a particular embodiment described herein.
Figure 5B:
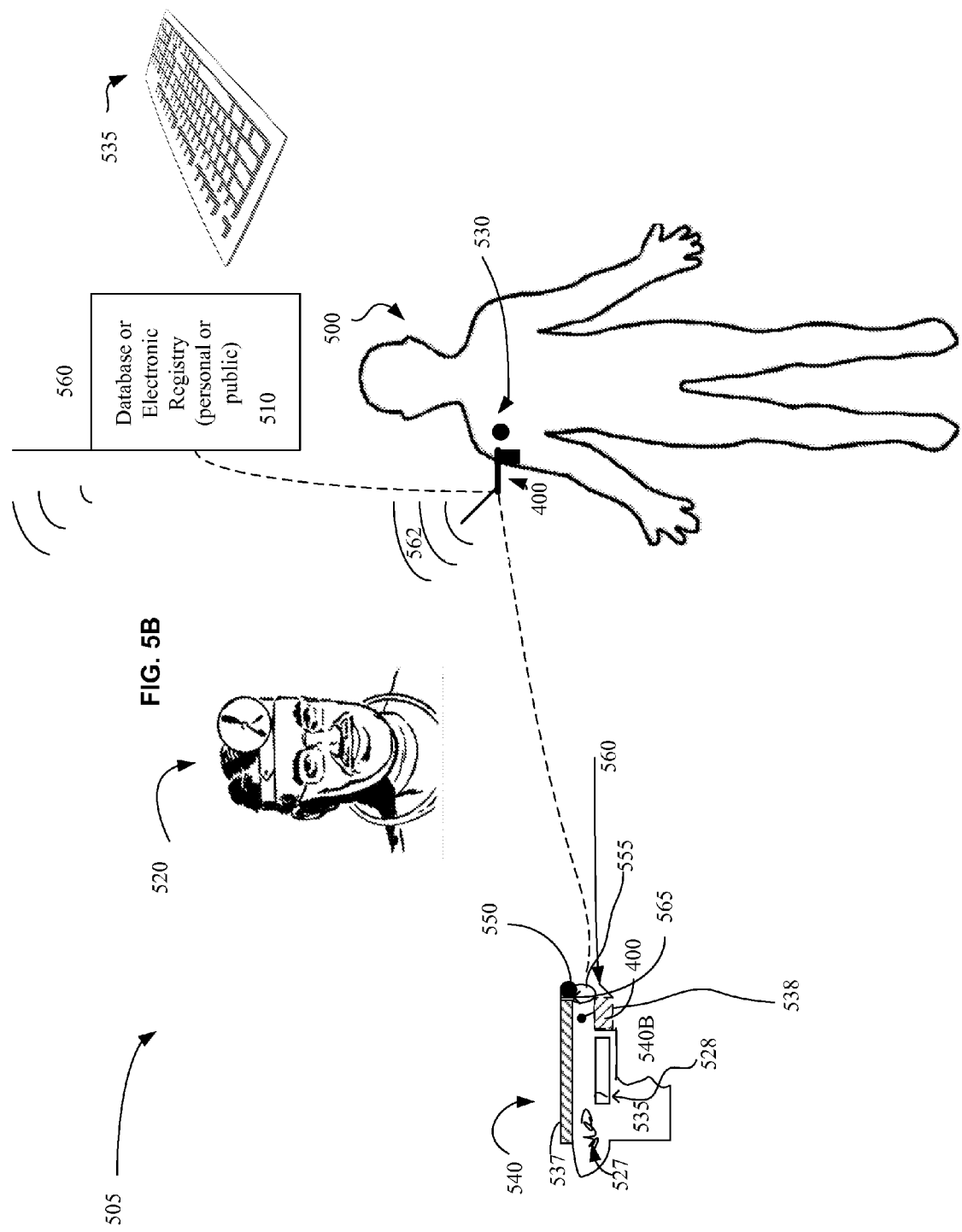
FIG. 5B illustrates a partial view of a particular embodiment described herein.
Figure 5C:
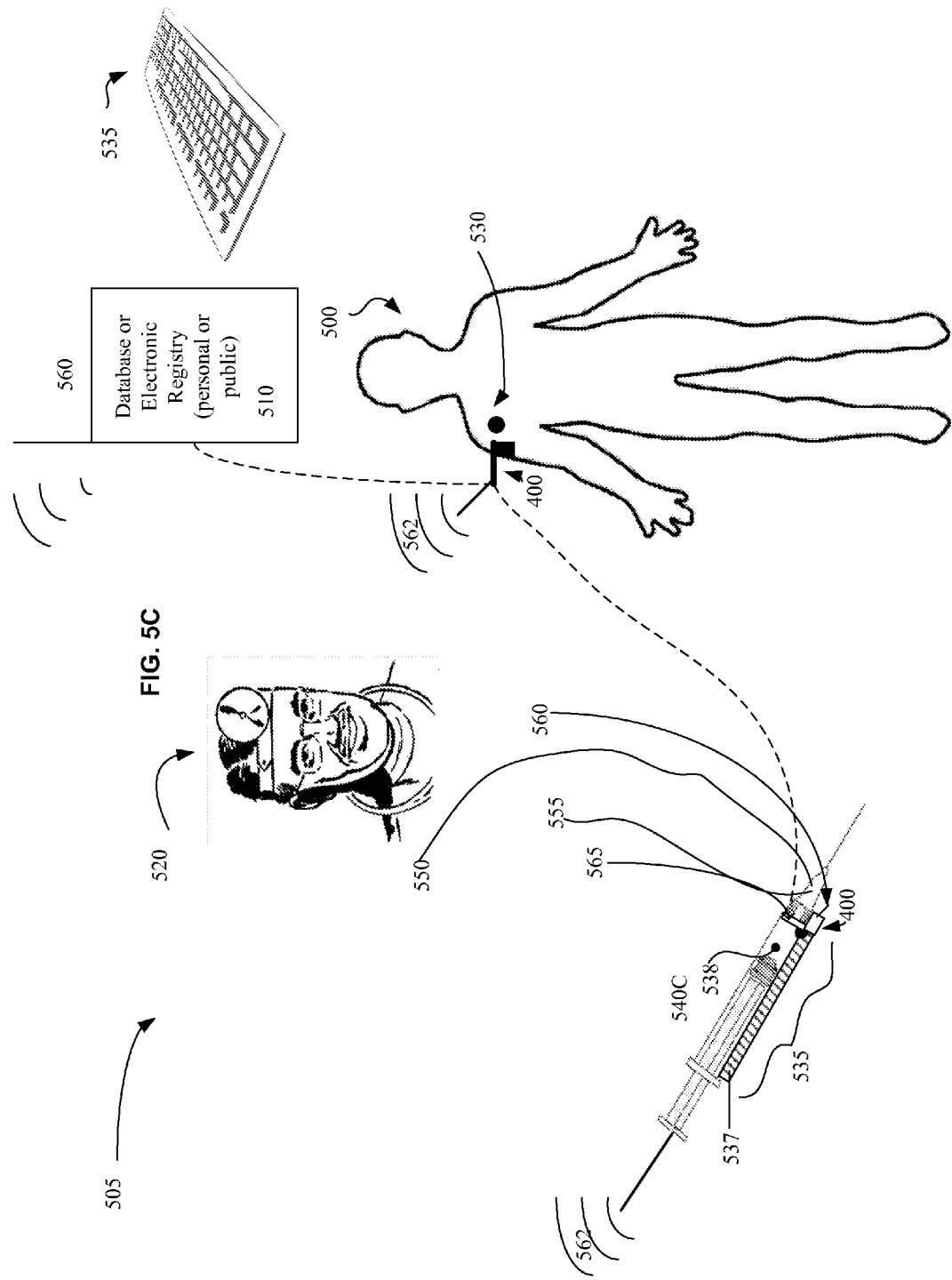
FIG. 5C illustrates a partial view of a particular embodiment described herein.

As depicted in FIGS. 5A, 5B, and 5C, in an embodiment, a system 505, includes a device 540 includes a housing 535, at least one first chamber 537 for containing the at least one information mark, at least one second chamber 538 for containing the at least one therapeutic agent, and means for administering 550 at least one information mark 530 to a subject 500. Thus, as depicted in the illustrations, 540A, 540B, and 540C each identify separate embodiments of a device 540 described in the application. In an embodiment, an information mark reader 400 includes means for receiving and/or transmitting at least one information signal from the information mark. In an embodiment, the device includes means for administering 555 at least one therapeutic agent. In an embodiment, the means for administering 550 at least one information mark is the same as the means for administering 555 at least one therapeutic agent. In an embodiment, the means for administering 550 at least one information mark is different than the means for administering 555 at least one therapeutic agent. In an embodiment, the device 540 includes at least one controllable output mechanism 565 as a component in a device 540 for administering at least one information mark. In an embodiment, (for example as in 540 B, 540C) the at least one information mark is contained in a separate chamber as the at least one therapeutic agent. In an embodiment (for example as in 540A) the at least one information mark is contained in the same chamber as the at least one therapeutic agent. In an embodiment, the at least one information mark 530 is administered to the surface of the subject 500 (e.g., skin). In an embodiment, the at least one information mark 530 is administered below the surface of the subject 500 (e.g., subdermally, subcutaneously, intra-muscularly, etc.). In an embodiment, the at least one controllable output mechanism for administering at least one information mark 565 is the same as the at least one controllable output mechanism for administering at least one therapeutic agent (e.g., see 540A, and 540C). In an embodiment, the at least one controllable output mechanism for administering at least one information mark 565 is different than the at least one controllable output mechanism for administering at least one therapeutic agent (e.g., 540B, 555, 565). In an embodiment, the means for administration of the at least one information mark 550 or at least one therapeutic agent includes at least one of a spring mechanism (527 of 540B), compressed gas (540A), or a power source mechanism (e.g., a battery) (not shown). In an embodiment, a trigger mechanism (for example, 528 of 540B) or other activation switch (not shown) dispenses at least one of the information mark or the therapeutic agent.

In an embodiment, the device 540 includes an electronic circuit system configured to be electrically coupled to the means for administering 550 at least one information mark. In an embodiment, the device 540 includes an electronic circuit system configured to be electrically coupled to the at least one controllable output mechanism 565.

In an embodiment, the device 540 can be any device suitable for administering at least one therapeutic agent or at least one information mark to a subject's body. In an embodiment, such device 540, includes but is not limited to auto-injectors, inhalers (540A), pen injectors, transdermal patches, pre-filled syringes, syringes (540C), catheters, vaccination guns (540B), stents, implantable vehicles, topical vehicles, pill dispensers, or other devices.

As described herein, the device 540 includes, in an embodiment, electronic circuitry for execution of various functions and activation of particular features described herein.

Also as described herein, in an embodiment, the device 540 includes a wireless communications system 562 configured to automatically transmit at least one parcel of information to another device, computer system, or electronic registry. In an embodiment, such wireless communication system 562 is configured to track subject compliance with medication administration (self-administration or administration by another entity).

In an embodiment, a health care provider 520 administers the information mark 530 just prior to, during, or subsequent to administration of other medical treatment (e.g., vaccination by a syringe or gun as indicated by 540, or inhaler, also 540). In an embodiment, at least some of the information included in the information mark 530 is transmitted 562, recorded, or stored in a database or electronic registry (personal or public) 510. In an embodiment, an input/output device 565 allows for entry of inputs by a user or for the presentation of information to the user. In an embodiment, a receiver 560 is configured to receive an information signal from the information mark 530. In an embodiment, the means for administering 550 at least one information mark 530 is further configured as means for "reading" at least one information mark 530.

As indicated in FIGS. 5A, 5B, and 5C, the dotted lines indicate that any one of the various disclosed device embodiments may be utilized for administration of an information mark 400 and optionally a therapeutic agent to a subject 500.

Various non-limiting embodiments are described herein as Prophetic Examples.

Prophetic Example 1

Methods and Device for Recording Medical Information in the Skin of a Child Receiving Recommended Vaccines A method using quantum dot microbeads is used to record medical information in the skin of a child who receives childhood vaccines. The child is approximately 1 year old and receives a recommended vaccine for measles, mumps and rubella. During or immediately after vaccination, the child is marked with quantum dot microbeads to indicate the date, the healthcare worker, the location, the vaccine product identity, the manufacturer, and the lot number. Quantum dot microbead markings are detected with a spectrofluorometer detector containing a light source, a photo-receptor for receiving light emitted by the illuminated quantum dots, and a spectroscopic analyzer for comparing variations in the intensity and wavelength of the emitted light. The detector communicates the spectral data to a computer where the data is stored and compared to predetermined spectral data for the quantum dot microbeads and the associated medical information.

The child is injected with vaccines using standard procedures and a marking of quantum dot microbeads is administered using a microneedle array immediately following vaccination. A combination vaccine for measles, mumps and rubella is injected subcutaneously in the arm of the child, according to the manufacturers' instructions (e.g., see M-M-R® II Product Sheet: available from Merck and Co., Inc., Whitehouse Station, N.J., which is incorporated herein by reference). Immediately following vaccination, the child is injected with quantum dot microbeads to record medical information about the vaccination. Microbeads containing quantum dots (ranging from 2-20 nm in diameter) are injected approximately 500 μm to 1000 μm below the skin surface, near the base of the epidermis. Quantum dots of different diameters, composed of CdSe capped with ZnS, emit light of different wavelengths. For example, quantum dots composed of a CdTe core and a CdSe shell may be created with emission wavelengths, ranging between 800 nm and 900 nm. Quantum dots with a diameter of approximately 10 nm are excited by 550 nm wavelength light and emit light at approximately 860 nm wavelength (e.g., see U.S. Pat. No. 7,181,266, which is incorporated herein by reference). Polymeric microbeads containing quantum dots with different diameters will display a composite emission profile composed of different wavelengths of light. The intensity of light emitted at each wavelength is proportional to the number of quantum dots present in the microbead having a particular diameter. Methods to construct optically encoded microbeads containing quantum dots are described (see e.g., Han et al., *Nature Biotechnology* 19: 631-635, 2001, which is incorporated herein by reference). Microbeads containing a mixture of quantum dots are fabricated from polyacrylamide hydrogels. Microbeads are fabricated from 10% (wt. %) acrylamide and 0.2% (wt. %) bisacrylamide, using a microfluidic device to create uniform beads approximately 130 μm in diameter. Methods and a microfluidic device to construct microbeads are described (see e.g., Shibata et al., *Proc. Natl. Acad. Sci. USA* 107: 17894-17898, 2010 which is incorporated herein by reference). Quantum dots with different core to shell dimensions and different diameters are synthesized by established procedures (see, e.g., U.S. Pat. No. 7,181,266 Ibid.) and are incorporated into microbeads at the time of polymerization. Incorporation of quantum dots into the microbeads allows detection of the encapsulated quantum dots injected in the dermis. For example, quantum dots, in dermal tissues, at a local concentration of approximately 1 μM, are detected through the skin (see e.g., Larson et al., *Science* 300: 1434-1436, 2003, which is incorporated herein by reference). Microbeads containing unique mixtures of quantum dots with characteristic emission spectra that vary in wavelength and intensity are injected beneath the epidermis in a pattern using a microneedle array.

Microbeads with unique fluorescent spectral signatures, as determined by a spectrofluorometer (available from Ocean Optics Inc., Dunedin, Fla.), are associated with data about the vaccination and the patient. For example, microbeads containing 1, 2 or 3 different quantum dots may emit light at 1, 2 or 3 wavelengths respectively, when excited by 550 nm light. Data about the microbeads (e.g., fluorescent spectra) are associated with medical information about the vaccine and the patient, and are entered into a computer for storage and future reference. For example:

Microbead 1 with an emission at 750 nm is associated with the M-M-R® II vaccine produced by Merck and Co., lot #XXX, expiration date.

Microbead 2 with emissions at 750 nm and 900 nm is associated with the age of the patient (e.g., 12 months) and the date of vaccination.

Microbead 3 with emissions at 750 nm, 900 nm and 1050 nm is associated with a recommended future vaccination with M-M-R® II vaccine, the recommended age and the recommended date for the future vaccination.

Microbead 4 with emissions at 750 nm, 900 nm (at reduced intensity, e.g., 0-30%) and 1050 nm may be associated with the site of the vaccination (e.g., school, clinic, hospital).

Additional microbeads with unique fluorescent spectral signatures may be fabricated by using quantum dots with distinct emission wavelengths and by varying the quantities of quantum dots so as to vary emission intensities. The use of 3 emission wavelengths and 10 different intensity levels theoretically yields approximately 1000 unique codes (see e.g., Han et al., Ibid.).

Following vaccination, a pattern of microbeads is injected beneath the epidermis of the patient on the wrist, using a microneedle array. Each unique microbead is injected by one microneedle from the array so as to allow detection of the microbead without interference from other microbeads. The microbeads are injected using an applicator comprising a hollow microneedle array that is connected to a reservoir. Hollow microneedle arrays may be fabricated using microfabrication technology adapted from the microelectronics industry. For example, silicon hollow microneedle arrays may be fabricated by etching holes through silicon wafers using deep reactive ion etching and then etching microneedles around the holes. See, e.g., McAllister et al., *Proc. Natl. Acad. Sci. USA*, 100: 13757-13760, 2003, which is incorporated herein by reference. Microneedle arrays (10×10) containing 100 microneedles in an area of 20×20 mm are constructed with conical microneedles, approximately 1000 μm in length and 300 μm in diameter, may be fabricated as shown by McAllister et al., Ibid. Alternatively, hollow microneedles may be fabricated from metals (e.g., Ni or NiFe) or polymers (e.g., polyglycolic acid and poly lactic acid) by using micromolds or by electroplating polymer microneedles with nickel as shown by McAllister et al., Ibid. Hollow microneedle arrays may be connected via a manifold to a mini-pump, to solenoid valve actuators, and to reservoirs containing microbead suspensions. Mini-pumps and solenoid valves are available from Parker-Hannifin, Precision Fluidics Division, Hollis, N.H. An applicator, comprising hollow microneedle arrays, solenoid valve actuators, a minipump, and reservoirs for the microbead suspensions, has a power source and micro-circuitry to control the injection of microbeads into the skin.

The microbead applicator is programmed by medical information entered in the computer to inject the correct, associated microbeads. For example, if a patient who is 12 months old receives the M-M-R® II vaccine and requires a future vaccination with M-M-R® II vaccine in 3 to 5 years, the information is entered into a computer and then transmitted to the applicator where microcircuitry selects the associated microbeads for injection. For example, microbeads 1-4 would be selected (see above for medical information associated with each microbead). Next, the microbead applicator is placed in contact with the patient's wrist and activated by pressing a button, which provides electric current from a lithium battery to drive the selected solenoid actuator valves and minipumps, delivering the selected microbead suspensions through distinct needles on the microneedle array. Each microbead suspension is injected at a separate, distinct position in the microneedle array to allow microbead detection without interference by neighboring microbeads.

Prophetic Example 2

Methods and Device for Detecting Medical Information in the Skin of a Child Entering School A child who is 6 years of age and entering school has his or her vaccination status checked. The child has previously received a first M-M-R® II vaccination, at age 1 year, marked by injection of microbeads beneath the epidermis of the child's wrist. The microbeads encode information about the vaccine, the child's vaccination status, and recommended future vaccinations. To verify the child's vaccination status prior to entering school, the microbeads in the wrist are analyzed with an apparatus placed over the skin that detects the wavelengths and intensities of light emitted from the microbeads. The apparatus includes a light source to illuminate the immediate area over each microbead injection and a photoreceptor that spectroscopically analyzes any emitted light. The apparatus has fiber optics, which transmit excitation wavelengths, such as ultraviolet light, visible light, near infrared light, and infrared light, to a local area over each microbead injection. The apparatus measures fluorescent light emanating through the skin immediately over the implanted microbeads, and records the wavelength and intensity of the emitted light. For example the apparatus may have a xenon light source rated at 300 Watt to excite the implanted microbeads with white light. Light emitted from the microbeads is detected with optical fibers connected to a spectrometer that detects the intensity of light at different wavelengths. An apparatus and methods for use in a dermal tissue comprising a light source, photo-receptor and/or spectral analyzer, as described (see e.g., U.S. Pat. No. 7,647,085, which is incorporated herein by reference). A portable spectrofluorometer, optical fibers, light source and associated software for measuring fluorescent light, are available from Ocean Optics Inc., Dunedin, Fla. (see e.g., the product sheet "Ocean Optics-QE65000-FL Scientific-Grade Spectrometer," which is incorporated herein by reference). Spectral data obtained from the implanted microbeads is transmitted to a computer and compared to reference data for the implanted microbeads. Spectral data is retained for the patient's health record and used for reference when the patient's vaccination status is interrogated.

Spectroscopy of the microbeads implanted in the student's wrist detects 4 different microbeads, each with a unique optical code. For example they may emit fluorescent light as described above (see Prophetic Example 1):

Microbead 1 with an emission at 750 nm
Microbead 2 with emissions at 750 nm and 900 nm
Microbead 3 with emissions at 750 nm, 900 nm and 1050 nm, and
Microbead 4 with emissions at 750 nm, 900 nm (at reduced intensity, e.g., 30%) and 1050 nm.

The spectral data is transmitted to a computer where the associated medical information is stored to translate the optical codes. The student's optical codes indicate that the student has not received a recommended second M-M-R® II vaccination and the school or healthcare provider may recommend the student receive the vaccination prior to entering school.

The student is given a second M-M-R® II vaccination, as required by the school system, and a fifth microbead is injected in the wrist of the student. Microbead 5 which emits light at 750 nm, 900 nm and 1050 nm (at reduced intensity, e.g., 30%) is associated with the second M-M-R® II vaccination including manufacturer, lot number, and expiration date. Additional microbeads with unique optical codes may be injected and associated with the vaccination date, recommended age for vaccination, age of the patient, name or position of healthcare worker administering the vaccine, and the site where vaccination occurred (e.g., the school, clinic, or office).

Prophetic Example 3

Methods and Device for Monitoring Psychiatric Treatment

A patient with bipolar disorder is prescribed anti-psychotic medication to control the patient's mood, and markings are placed under the patient's skin to indicate administration of the medication. The patient is treated for acute mania and placed on a maintenance regimen of an atypical antipsychotic. After each daily dose, the patient is injected on the wrist with optically encoded quantum dots using a microneedle array. The quantum dots are incorporated in microbeads, which are injected just beneath the epidermis. The quantum dots are detected with a fluorospectrometer, and the fluorescent spectra are transmitted to a computer for decoding. The optically encoded quantum dots indicate to a caregiver the medications administered, the dates of administration, and future recommended doses, as well as patient-specific information.

The patient with bipolar disease is given an antipsychotic daily to control his or her mood, and a marking of quantum dot microbeads is administered each day using a microneedle array. A maintenance regimen of 30 mg daily of the antipsychotic aripiprazole (also known as Abilify® available from Bristol-Myers Squibb, New York, N.Y.) is given to the patient (see e.g., Keck et al., *J. Clin. Psychiatry* 68: 1480-1491, 2007, which is incorporated herein by reference). Immediately following administration of each dose, the patient is injected with microbeads containing quantum dots to record medical information about the medication and the patient. Microbeads containing quantum dots (ranging from 2-20 nm in diameter) are injected approximately 300 μm to 1000 μm below the skin surface near the base of the epidermis. Quantum dots of different diameters emit light of different wavelengths. For example, quantum dots composed of a CdTe core and a CdSe shell may be created with emission wavelengths ranging between 800 nm and 900 nm. Quantum dots with a diameter of approximately 10 nm may be excited by 550 nm wavelength light and emit light at approximately 860 nm wavelength (e.g., see U.S. Pat. No. 7,181,266, which is incorporated herein by reference). Polymeric microbeads containing quantum dots with different diameters will display a composite emission profile composed of different wavelengths of light. The intensity of light emitted at each wavelength is proportional to the number of quantum dots having a particular diameter that are present in the microbead. Methods to construct optically encoded microbeads containing quantum dots are described (see e.g., Han et al., Nature Biotechnology 19: 631-635, 2001, which is incorporated herein by reference). Microbeads containing a mixture of quantum dots may be fabricated from polyacrylamide hydrogels. Microbeads are fabricated from 10% (wt. %) acrylamide and 0.2% (wt. %) bisacrylamide, using a microfluidic device to create uniform beads approximately 130 μm in diameter. Methods and a microfluidic device to construct microbeads are described (see e.g., Shibata et al., *Proc. Natl. Acad. Sci. USA* 107: 17894-17898, 2010, which is incorporated herein by reference). Quantum dots with different core to shell dimensions and different diameters are synthesized by established procedures (see e.g., U.S. Pat. No. 7,181,266 Ibid.) and incorporated into microbeads at the time of polymerization. Incorporation of quantum dots into the microbeads allows detection of the encapsulated quantum dots injected in the dermis. For example, quantum dots in dermal tissues, at a local concentration of approximately 1 μM, are detected through the skin (see e.g., Larson et al., *Science* 300: 1434-1436, 2003, which is incorporated herein by reference). Microbeads containing unique mixtures of quantum dots with characteristic emission spectra that vary in wavelength and intensity are injected beneath the epidermis in a pattern using a microneedle array.

Microbeads with unique fluorescent spectral signatures as determined by a spectrofluorometer (available from Ocean Optics Inc., Dunedin, Fla.) are associated with data about administration of medication and the patient. For example, microbeads containing 1, 2 or 3 different quantum dots may emit light at 1, 2 or 3 wavelengths respectively, when excited by 550 nm light. Microbeads with unique fluorescent spectral signatures may be fabricated by using quantum dots with distinct emission wavelengths, and by varying the quantities of quantum dots so as to vary emission intensities. The use of 3 emission wavelengths and 10 different intensity levels theoretically yields approximately 1000 unique codes (see e.g., Han et al., Ibid.). Data about the microbeads (e.g., fluorescent spectra) are associated with medical information about the drug(s) administered, including the dose, date of administration, and the patient's identity. The fluorescent spectra and associated medical information are entered into a computer for storage and future reference. For example, a microbead with a unique fluorescence spectra may be associated with each day's dose of aripiprazole by associating the date, drug, and patient identity with a unique microbead each day.

For example, following administration of 30 mg of aripiprazole, approximately 20 µl of a suspension of a unique microbead, containing quantum dots, at a final concentration of 10 µM, is injected beneath the epidermis of the patient on the wrist using a microneedle array. Each microbead suspension is injected by one microneedle from the array, so as to allow detection of the microbead without interference from other microbeads. The microbeads are injected using an applicator comprising a hollow microneedle array that is connected to a reservoir. Hollow microneedle arrays may be fabricated using microfabrication technology adapted from the microelectronics industry. For example, silicon hollow microneedle arrays may be fabricated by etching holes through silicon wafers using deep reactive ion etching and then etching microneedles around the holes. See, e.g., McAllister et al., *Proc. Natl. Acad. Sci. USA*, 100: 13757-13760, 2003, which is incorporated herein by reference.

Microneedle arrays (10×10) containing 100 microneedles in an area of 20×20 mm are constructed with conical microneedles approximately 100 µm to 1000 µm in length and 300 µm in diameter may be fabricated as shown by McAllister et al., Ibid. Alternatively, hollow microneedles may be fabricated from metals (e.g., Ni or NiFe) or polymers (e.g., polyglycolic acid and poly lactic acid) by using micromolds or by electroplating polymer microneedles with nickel, as shown by McAllister et al., Ibid. Hollow microneedle arrays may be connected via a manifold to a mini-pump, to solenoid valve actuators, and to reservoirs containing microbead suspensions. Mini-pumps and solenoid valves are available from Parker-Hannifin, Precision Fluidics Division, Hollis, N.H. An applicator, comprising hollow microneedle arrays, solenoid valve actuators, a minipump, and reservoirs for the microbead suspensions, has a power source and micro-circuitry to control the injection of microbeads into the skin.

The microbead applicator is programmed to inject the correct, associated microbead. For example, if the psychiatric patient A receives 30 mg aripiprazole on Tuesday, May 3, 2011, the information is entered into a computer and then transmitted to the applicator, where microcircuitry selects the associated microbead for injection. The selected microbead suspension is injected from a unique address in the microneedle array. The microbead applicator is placed in contact with the patient's wrist and activated by pressing a button, which provides electric current from a lithium battery to drive the selected solenoid actuator valves and minipumps, delivering the selected microbead suspension. Each microbead suspension is injected at a separate, distinct position in the microneedle array to allow microbead detection independent from that of neighboring microbeads.

To verify that patient A has received his or her apiprazole today or any previous day, the microbeads in the patient's wrist are analyzed with an apparatus placed over the skin that detects the wavelengths and intensities of light emitted from the implanted microbeads. The apparatus includes a light source to illuminate the immediate area over each microbead injection and a photoreceptor which spectroscopically analyzes any emitted light. For example, the apparatus may have a xenon light source rated at 300 Watt to excite the implanted microbeads with white light. The apparatus has fiber optics which transmit excitation light to a local area over each microbead injection. The apparatus measures fluorescent light, for example at 850 nm, emanating from the microbead through the skin immediately over the implanted microbead, with optical fibers connected to a spectrometer. The spectrometer transmits the wavelength and intensity data of the emitted light to a computer, where the optical code is translated to the corresponding medical information. An apparatus and methods for use in a dermal tissue comprising a light source, photo-receptor, and spectral analyzer as described (see e.g., U.S. Pat. No. 7,647,085, which is incorporated herein by reference). A portable spectrofluorometer, optical fibers, light source, and associated software for measuring fluorescent light, are available from Ocean Optics Inc., Dunedin, Fla. (see e.g., the product sheet: "Ocean Optics-QE65000-FL Scientific-Grade Spectrometer" which is incorporated herein by reference). Spectral data obtained from the implanted microbeads is transmitted to a computer and compared to reference data for the implanted microbeads. Spectral data is retained for the patient's health record, and used for reference when the patient's medication status is interrogated.

Prophetic Example 4

Methods and Device for Monitoring Adherence to Antihypertensive Therapy

An elderly patient with chronic hypertension is prescribed antihypertensives. To monitor the patient's adherence to the treatment plan, the patient is marked with a magnetic marking system to record information on the patient's body that indicates the status of medications administered. The magnetic marking system is composed of magnetic particles that are implanted in the skin in a pattern that can be detected visually and with a laser scanner. The magnetic particles are moved in the skin using a strong magnet to change the color pattern of the particles, and past, present and future doses of medication are indicated by the pattern of the particles.

The patient is prescribed a treatment plan to control hypertension and is provided with a magnetic marking system to monitor adherence to the treatment plan. To control hypertension, a "beta blocker", propranolol, is prescribed as 80 mg tablets to be taken twice a day, and a diuretic, hydrochlorothiazide, is prescribed as 12.5 mg tablets taken once a day. (See FIG. 1).

To monitor adherence to the treatment plan, the patient is injected in the skin of the wrist with magnetic microparticles containing chromophores and having an inert polymer coating. Magnetic microparticles composed of $Fe_3O_4$, approximately 1 µm in diameter, are available from Bangs Laboratories Inc., Fishers, Ind. The magnetic microparticles are coated with the chromophores FD&C Blue No. 1 and FD&C Red No. 3 to create blue and red magnetic particles, respectively. A transparent, inert, biocompatible coating (e.g., Epo-Tek®301 available from Epoxy Technology, Billerica, Mass.) is applied to protect the particles, and the particles are suspended in a carrier such as 20% (w/w) glycerin. The particles may also be non-magnetic, and may be colored with a chromophore (e.g., FD&C Yellow No. 6) to create yellow particles that are not influenced by a magnetic field. Methods and compositions for creating magnetic tissue markings are described (see e.g., U.S. Pat. No. 7,344,587, which is incorporated herein by reference).

A pattern of colored magnetic markings is injected on the wrist immediately beneath the epidermis of the patient (approximately 100 µm to 300 µm beneath the skin). An oscillating tattoo machine with a needle array (e.g., Spaulding Tattoo Machine available from Spaulding and Rogers, Albany, N.Y.) may be used to inject the particles and create a pattern that encodes dosing information.

A pattern of colored magnetic and nonmagnetic particles is implanted under the patient's epidermis to monitor treatment with multiple drugs. To indicate twice daily dosing with 80 mg of propranolol, two rows of dots (with 7 dots per row) are injected using a mix of magnetic blue particles and nonmagnetic yellow particles to create green dots. To indicate daily dosing with 15 mg of hydrochlorothiazide, one row of 7 ovals is injected using a mix of magnetic red particles and non-magnetic yellow particles to create brown ovals. See FIG. 1.

To indicate administration of a dose of propranolol, a handheld electromagnet is passed over a single green dot (e.g., green dot 1 in row 1 in FIG. 1) to cause migration of the blue magnetic particles within the dot, thereby revealing a yellow dot. Thus, the first dose of propranolol has been consumed on the first day of the week (e.g., designated Monday). Methods and devices to move magnetic particles within the skin are described (see U.S. Pat. No. 7,344,587, Ibid.). To indicate administration of hydrochlorothiazide on the first day of the week, the electromagnet is passed over the first brown oval, thus moving the red magnetic particles and revealing a yellow oval. Administration of succeeding doses of propranolol and hydrochlorothiazide are accompanied by application of the electromagnet to the corresponding dots and ovals, respectively. Visual inspection of the magnetic markings identifies the status of the treatment plan.

After 7 days of complete adherence to the treatment plan, all dots and ovals should be yellow. The following week, administration of propranolol and hydrochlorothiazide are indicated by applying a magnetic field to return the blue and red magnetic particles over the yellow dots and ovals, to create green dots and brown ovals respectively.

The colored markings in the skin may be detected by a device that detects light absorbed and/or reflected from the markings and transmits the resulting cumulative data to a computer system for storage and analysis. A CCD camera may be used to capture images of the colored markings, and to transmit the images of the markings to a computer. Methods and devices for detecting chromophores in dermal tissue are described (see e.g., U.S. Pat. No. 7,647,085, Ibid.). For example, the green dots and brown ovals indicating treatment with anti-hypertensive drugs can be imaged with a CCD camera, e.g., a QIClick Digital CCD Camera available from Q Imaging, Surrey, BC, Canada (see a QIClick datasheet, which is incorporated herein by reference), connected to a computer. Images of the colored tissue markings are captured and analyzed by the computer system and the date, time, and medications administered are stored in the computer with the images. The computer system also stores the treatment plan, as well as past and present doses of medication that are administered. Based on current images of the magnetic markings, the computer system also predicts future doses of medication.

Prophetic Example 5

Device and Methods for Recording and Rewarding Vaccination

A subject is vaccinated with an influenza vaccine, and a marking is made in the skin with a dielectric ink to identify the subject and to record the vaccination. The dielectric ink is detected using handheld sensors to detect microwaves reflected from the dielectric ink pattern. Signals from the sensor are relayed to a computer and analyzed to verify that the subject has been vaccinated and is entitled to a reward. The device and methods are useful for monitoring adherence to a treatment plan, to plan additional vaccinations, and/or to activate a reward system for compliance with the vaccination protocol.

An elderly subject is vaccinated with a seasonal influenza vaccine and marked with a dielectric ink to record medical information in the skin about the vaccine. The vaccine is injected with a microneedle as described (See e.g., Holland et al., *J. Inf. Dis.* 198: 650-658, 2008, which is incorporated herein by reference). The intradermal vaccine may be a trivalent inactivated split-virion influenza vaccine formulated according to season-appropriate strain recommendations (e.g., A/New Caledonia/20/99 [H1N1], A/Wellington/1/2004 [H3N2], and B/Jiangsu/10/2003), from monovalent lots generally used to prepare the licensed vaccine Vaxigrip (Sanofi Pasteur, Swiftwater, Pa.). The intradermal vaccine, also produced by Sanofi Pasteur (Swiftwater, Pa.), contains approximately 15 to 21 µg of hemagglutinin (HA) per strain per 0.1-mL dose, and is administered in the deltoid region using the BD Microinjection System (Becton Dickinson, Franklin Lakes, N.J.).

Immediately after microinjection of the influenza vaccine, a dielectric ink marking is applied to the wrist area of the subject. Methods to apply dielectric ink markings to the skin are described (see e.g., U.S. Patent App. Pub. No. 2009/0039158, which is incorporated herein by reference). The dielectric ink is applied in a pattern that encodes medical information about the subject and the vaccination. The encoded information may include the subject's name, birthdate, and insurance carrier; the vaccine's identity, lot number, and producer; the date of the vaccination; and the identity of the healthcare giver. The medical information, and the corresponding dielectric ink markings are entered into a computer. For example, a dielectric ink is formed from a biocompatible ceramic, sodium potassium niobate ($Na_{0.5}K_{0.5}(NbO3)$) (see e.g., Bomlai, Proceedings of the Thailand Materials Science and Technology Conference, CO5, 2008, and U.S. Pat. No. 6,526,984, each of which is incorporated herein by reference). Potassium niobate suspended as a fine powder in a fluid solvent, such as water, dimethyl sulfoxide, or 2-propanol, and an inkjet printer may be used to create a pattern that encodes medical information on the skin (see e.g., U.S. Patent App. Pub. No. 2003/0065294, which is incorporated herein by reference). A microwave readable barcode with dielectric elements encoding 96 bits may be printed in a width of approximately 28 mm. Alternatively, for a long-term or permanent marking, the dielectric elements may be injected into the dermis. (See e.g., U.S. Patent App. Pub. No. 2009/0039158, Ibid.).

The dielectric pattern may form a representation (e.g., bar code) made up of bars with varying width, height, vertical distribution, and orientation, or the pattern may form a binary code (e.g., zeros and ones). The dielectric markings are read by irradiation with a microwave transmitter operating at approximately 1.0 TeraHerz frequency and 300 µm wavelength, followed by detection of the attenuated portion of the signal resulting after microwaves strike the dielectric elements and scattering occurs.

The microwave signal is detected by a sensor that may be an antenna connected to the microwave transmitter. The sensor also includes a processor capable of decoding the encoded information present in the dielectric pattern. The information processed by the sensor is transmitted to a computer for storage and analysis. Systems for detecting dielectric barcodes are described (see e.g., U.S. Patent App. Pub. No. 2009/0039158, Ibid.). The dielectric pattern printed on the subject at the time he or she received a flu vaccine may be interrogated remotely by a sensor, and the information obtained may be transmitted to a third party.

Compliance with a recommended vaccination schedule may be rewarded by a third party. For example, an insurance company may receive information from a remote dielectric marking sensor in a clinic waiting room or in a public place (e.g., airport, shopping mall), certifying that a subject has received an influenza vaccination. The insurance company may reward the subject by providing a credit to the subject's credit card for any medical bills incurred in the clinic. Alternatively, the insurance company may reward the subject by awarding credits at the shopping mall or travel miles on the patient's credit card.

The vaccination history and reward history for the subject are stored in a database in the system's computer, and are updated when new vaccinations, new dielectric markings, and new rewards are detected by handheld sensors. Detection may occur at the time of new vaccination or later, for example by a remote sensor in a public place. The stored information may be used by a third party, for example by an insurance company for billing purposes, or by an insurance company or public health system for statistical purposes.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system, comprising:
   a device including at least one first controllable output mechanism operably coupled to electronic circuitry and configured for administering at least one therapeutic agent to a subject, the at least one first controllable output mechanism including one or more of a needle, inhaler, transdermal patch, microneedle, needle array, inkjet injector, or needle-less injector; and
   at least one programmable microneedle array operably coupled to electronic circuitry, and configured for administering at least one information mark as a pattern of particles, to the subject in conjunction with administering the at least one therapeutic agent, and operably coupled to at least two reservoirs containing microbead suspensions; and
   at least one information mark reader operably coupled to electronic circuitry;
   wherein the system includes a computing device operably coupled to medical treatment determination electronic circuitry configured to determine a subsequent medical treatment based on an information signal received from an information mark(s) previously administered to the subject.

2. The system of claim 1, wherein the at least one information mark includes at least one parcel of information that is unique to the subject receiving the information mark.

3. The system of claim 2, wherein the at least one parcel of information that is unique to a subject includes information related to the at least one dose of the therapeutic agent.

4. The system of claim 1, wherein the information mark reader is configured to receive information related to at least one information mark including at least one pattern.

5. The system of claim 1, wherein the device is portable.

6. The system of claim 1, wherein the device is handheld.

7. The system of claim 1, wherein the information mark reader is configured to read the at least one information mark.

8. The system of claim 1, wherein the information mark reader includes an optical sensor.

9. The system of claim 8, wherein the optical sensor is configured for sensing at last one information mark previously administered to the subject.

10. The system of claim 8, wherein an optical sensor is configured for sensing at least one pattern of two or more information marks.

11. The system of claim 1, wherein the information mark reader includes a receiver configured for receiving an information signal from at least one information mark previously administered to the subject.

12. The system of claim 11, wherein the information mark previously administered to a subject includes at least one parcel of information relating to previous therapeutic administration, biometric information, or other medical or personal information related to the subject.

13. The system of claim 1, wherein the subsequent medical treatment includes administering at least one additional therapeutic agent.

14. The system of claim 1, wherein the subsequent medical treatment includes refraining from administering a therapeutic agent.

15. The system of claim 1, wherein the particles include at least one of magnetic particles, colored non-magnetic particles, or polymeric microbeads.

16. A device, comprising:
   at least one first controllable output mechanism operably coupled to electronic circuitry and configured for administering at least one therapeutic agent to a subject, the at least one first controllable output mechanism including one or more of a needle, inhaler, transdermal patch, microneedle, needle array, inkjet injector, or needle-less injector; and
   at least one programmable microneedle array operably coupled to electronic circuitry, and configured for administering at least one information mark as a pattern of particles, to the subject in conjunction with administering the at least one therapeutic agent, and operably coupled to at least two reservoirs containing microbead suspensions; and
   at least one information mark reader operably coupled to electronic circuitry;
   wherein the device is operably coupled to medical treatment determination electronic circuitry configured to determine a subsequent medical treatment based on an information signal received from an information mark(s) previously administered to the subject.

17. The device of claim 16, wherein the at least one information mark includes at least one parcel of information that is unique to the subject receiving the information mark.

18. The device of claim 17, wherein the at least one parcel of information that is unique to the subject includes information related to the at least one dose of the therapeutic agent.

19. The device of claim 16, wherein the information mark reader is configured to receive information related to at least one information mark including at least one pattern.

20. The device of claim 16, wherein the device is portable.

21. The device of claim 16, wherein the device is handheld.

22. The device of claim 16, wherein the device is in electronic communication with a computing system.

23. The device of claim 16, wherein the information mark reader is configured to read the at least one information mark.

24. The device of claim 16, wherein the information mark reader includes an optical sensor.

25. The device of claim 24, wherein the optical sensor is configured for sensing at last one information mark previously administered to the subject.

26. The device of claim 24, wherein an optical sensor is configured for sensing at least one pattern of two or more information marks.

27. The device of claim 16, wherein the information mark reader includes a receiver configured for receiving an information signal from at least one information mark previously administered to a subject.

28. The device of claim 27, wherein the information mark previously administered to the subject includes at least one parcel of information relating to previous therapeutic administration, biometric information, or other medical or personal information related to the subject.

29. The device of claim 16, wherein the subsequent medical treatment includes administering at least one additional therapeutic agent.

30. The device of claim 16, wherein the subsequent medical treatment includes refraining from administering a therapeutic agent.

31. The device of claim 16, wherein the particles include at least one of magnetic particles, colored non-magnetic particles, or polymeric microbeads.

* * * * *